US012683623B2

(12) United States Patent
Hwang et al.

(10) Patent No.: US 12,683,623 B2
(45) Date of Patent: Jul. 14, 2026

(54) METHODS AND APPARATUSES FOR OPERATING ANALOG-TO-DIGITAL CONVERTERS IN AN ULTRASOUND DEVICE WITH TIMING DELAYS

(71) Applicant: BFLY OPERATIONS, INC., Guilford, CT (US)

(72) Inventors: Sewook Hwang, Branford, CT (US); Nevada J. Sanchez, Guilford, CT (US)

(73) Assignee: BFLY OPERATIONS, INC., Burlington, MA (US)

( * ) Notice: Subject to any disclaimer, the term of this patent is extended or adjusted under 35 U.S.C. 154(b) by 1188 days.

(21) Appl. No.: 17/109,946

(22) Filed: Dec. 2, 2020

(65) Prior Publication Data

US 2021/0167791 A1     Jun. 3, 2021

Related U.S. Application Data

(60) Provisional application No. 62/943,183, filed on Dec. 3, 2019.

(51) Int. Cl.
| | |
|---|---|
| *H03M 1/12* | (2006.01) |
| *A61B 8/00* | (2006.01) |
| *A61N 7/00* | (2006.01) |

(52) U.S. Cl.
CPC ......... *H03M 1/1245* (2013.01); *A61B 8/5269* (2013.01); *A61B 8/54* (2013.01); *A61N 7/00* (2013.01)

(58) Field of Classification Search
CPC ............... H03M 1/123; H03M 1/1245; H03M 1/124–128; A61B 8/085; A61B 8/12; A61B 8/4444; A61B 8/5269; A61B 8/54; A61N 7/00
See application file for complete search history.

(56) References Cited

U.S. PATENT DOCUMENTS

| | | | | |
|---|---|---|---|---|
| 4,983,970 | A | * | 1/1991 | O'Donnell ........... G10K 11/346 |
| | | | | 341/122 |
| 8,852,103 | B2 | | 10/2014 | Rothberg et al. |
| 9,067,779 | B1 | | 6/2015 | Rothberg et al. |
| 9,229,097 | B2 | | 1/2016 | Rothberg et al. |
| 9,242,275 | B2 | | 1/2016 | Rothberg et al. |

(Continued)

FOREIGN PATENT DOCUMENTS

| | | | | | |
|---|---|---|---|---|---|
| JP | H08322837 | A | * | 12/1996 | ............... A61B 8/00 |
| KR | 101636234 | B1 | * | 7/2016 | ........... A61B 8/4483 |

*Primary Examiner* — Yuqing Xiao
*Assistant Examiner* — Chia-Ling Chen
(74) *Attorney, Agent, or Firm* — Carter, DeLuca & Farrell, LLP; Vadim Vapnyar

(57) ABSTRACT
Aspects of the technology described herein relate to an ultrasound device having a first analog-to-digital converter (ADC) configured to operate with a first ADC clock signal having a first timing delay and a second ADC configured to operate with a second ADC clock signal having a second timing delay. The first timing delay and the second timing delay may be different. The ultrasound device may further include delay control circuitry configured to control direct digital synthesis (DDS) circuitry to implement a first delay in ultrasound data from the first ADC and a second delay in ultrasound data from the second ADC. The first delay may correct for the first timing delay and the second delay may correct for the second timing delay.

23 Claims, 13 Drawing Sheets

(56)                    References Cited

U.S. PATENT DOCUMENTS

| | | | |
|---|---|---|---|
| 9,499,392 B2 | 11/2016 | Rothberg et al. | |
| 9,505,030 B2 | 11/2016 | Rothberg et al. | |
| 9,521,991 B2 | 12/2016 | Rothberg et al. | |
| 9,533,873 B2 | 1/2017 | Rothberg et al. | |
| 9,592,030 B2 | 3/2017 | Rothberg et al. | |
| 9,592,032 B2 | 3/2017 | Rothberg et al. | |
| 10,175,347 B2 | 1/2019 | Chen et al. | |
| 10,187,020 B2 | 1/2019 | Chen et al. | |
| 10,196,261 B2 | 2/2019 | Rothberg et al. | |
| 10,695,034 B2 | 6/2020 | Ralston et al. | |
| 10,720,936 B1* | 7/2020 | Xu | H03M 1/121 |
| 10,755,692 B2 | 8/2020 | Ralston et al. | |
| 10,856,840 B2 | 12/2020 | Rothberg et al. | |
| 10,859,687 B2 | 12/2020 | Bao et al. | |
| 2007/0232917 A1* | 10/2007 | Bae | G01N 29/07 |
| | | | 600/447 |
| 2008/0242992 A1* | 10/2008 | Criton | G01S 15/8995 |
| | | | 600/447 |
| 2009/0045994 A1* | 2/2009 | Drummy | G01N 29/262 |
| | | | 341/155 |
| 2011/0055447 A1 | 3/2011 | Costa | |
| 2014/0243614 A1 | 8/2014 | Rothberg et al. | |
| 2015/0031999 A1* | 1/2015 | Willsie | A61B 8/56 |
| | | | 600/437 |
| 2015/0280841 A1* | 10/2015 | Gudovskiy | H04L 27/22 |
| | | | 375/226 |
| 2017/0280079 A1* | 9/2017 | Fu | H04N 25/76 |
| 2017/0281138 A1 | 10/2017 | Bao et al. | |
| 2017/0307740 A1 | 10/2017 | Ralston et al. | |
| 2017/0307741 A1 | 10/2017 | Ralston et al. | |
| 2017/0360399 A1 | 12/2017 | Rothberg et al. | |
| 2018/0070917 A1 | 3/2018 | Rothberg et al. | |
| 2018/0376253 A1 | 12/2018 | Lutsky et al. | |
| 2019/0001159 A1 | 1/2019 | Chen et al. | |
| 2019/0069842 A1 | 3/2019 | Rothberg et al. | |
| 2019/0072671 A1* | 3/2019 | Nikolov | G01S 15/8993 |
| 2019/0142387 A1 | 5/2019 | Chen et al. | |
| 2019/0227165 A1* | 7/2019 | Savord | G01S 7/5208 |
| 2019/0282207 A1 | 9/2019 | Chen et al. | |
| 2019/0343484 A1 | 11/2019 | Rothberg et al. | |
| 2019/0343485 A1* | 11/2019 | Shepard | A61N 7/00 |
| 2020/0022677 A1* | 1/2020 | Takano | A61B 8/4444 |
| 2020/0315586 A1 | 10/2020 | Sanchez | |
| 2020/0315592 A1 | 10/2020 | Soleimani et al. | |
| 2021/0007717 A1* | 1/2021 | Savord | A61B 8/4444 |

* cited by examiner

FIG. 5

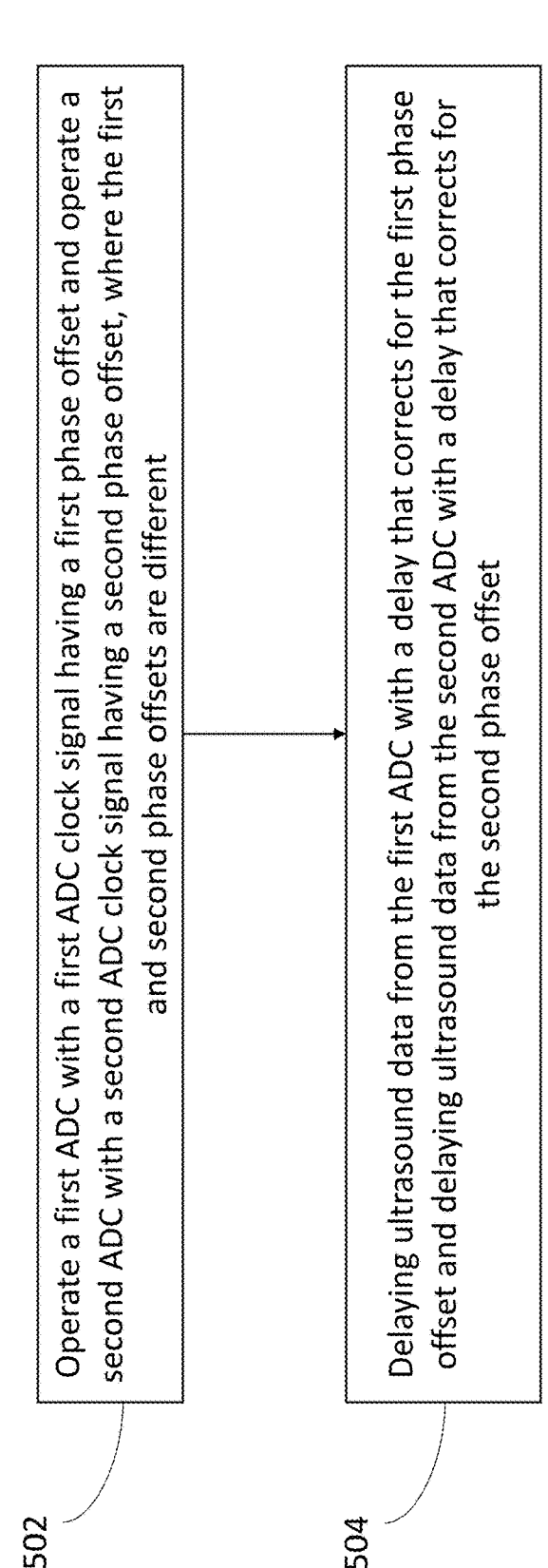

500

502

Operate a first ADC with a first ADC clock signal having a first phase offset and operate a second ADC with a second ADC clock signal having a second phase offset, where the first and second phase offsets are different

504

Delaying ultrasound data from the first ADC with a delay that corrects for the first phase offset and delaying ultrasound data from the second ADC with a delay that corrects for the second phase offset

1000

1200

METHODS AND APPARATUSES FOR OPERATING ANALOG-TO-DIGITAL CONVERTERS IN AN ULTRASOUND DEVICE WITH TIMING DELAYS

CROSS-REFERENCE TO RELATED APPLICATIONS

This application claims the benefit under 35 U.S.C. § 119(e) of U.S. Provisional Application Ser. No. 62/943,183, filed on Dec. 3, 2019, and entitled "METHODS AND APPARATUSES FOR OPERATING ANALOG-TO-DIGI-TAL CONVERTERS IN AN ULTRASOUND DEVICE WITH TIMING DELAYS", which is hereby incorporated by reference herein in its entirety.

FIELD

Generally, the aspects of the technology described herein relate to ultrasound devices. Some aspects relate to methods and apparatuses for operating analog-to-digital converters with timing delays.

BACKGROUND

Ultrasound probes may be used to perform diagnostic imaging and/or treatment, using sound waves with frequen-cies that are higher than those audible to humans. Ultrasound imaging may be used to see internal soft tissue body structures. When pulses of ultrasound are transmitted into tissue, sound waves of different amplitudes may be reflected back towards the probe at different tissue interfaces. These reflected sound waves may then be recorded and displayed as an image to the operator. The strength (amplitude) of the sound signal and the time it takes for the wave to travel through the body may provide information used to produce the ultrasound image. Many different types of images can be formed using ultrasound devices. For example, images can be generated that show two-dimensional cross-sections of tissue, blood flow, motion of tissue over time, the location of blood, the presence of specific molecules, the stiffness of tissue, or the anatomy of a three-dimensional region.

SUMMARY

According to one aspect of the application, an ultrasound device includes a first analog-to-digital converter (ADC) configured to operate with a first ADC clock signal having a first timing delay and a second ADC configured to operate with a second ADC clock signal having a second timing delay different than the first timing delay.

In some embodiments, the first ADC is configured to operate with the first ADC clock signal and the second ADC is configured to operate with the second ADC clock signal, such that sample and hold operations of the first ADC and the second ADC start at times that are different by a fraction of a sampling clock period. In some embodiments, the first ADC is in one ultrasound processing unit (UPU) and the second ADC is in another UPU. In some embodiments, the first ADC and the second ADC are in a single ultrasound processing unit (UPU).

In some embodiments, the ultrasound device further includes first clocking circuitry configured to provide the first ADC clock signal to the first ADC and second clocking circuitry configured to provide the second ADC clock signal to the second ADC. In some embodiments, the ultrasound device further includes clocking circuitry configured to provide the first ADC clock signal to the first ADC and the second ADC clock signal to the second ADC.

In some embodiments, the first ADC clock signal and the second ADC clock signal are derived from a system clock. In some embodiments, the first ADC clock signal and the second ADC clock signal are generated by a phase-locked loop (PLL). In some embodiments, the first ADC clock signal and the second ADC clock signal have a same frequency.

In some embodiments, the ultrasound device further includes first direct digital synthesis (DDS) circuitry, first delay control circuitry configured to control the first DDS circuitry to implement a first delay in ultrasound data from the first ADC, second DDS circuitry, and second delay control circuitry configured to control the second DDS circuitry to implement a second delay in ultrasound data from the second ADC, where the first delay and the second delay are different. In some embodiments, the ultrasound device further includes direct digital synthesis (DDS) cir-cuitry and delay control circuitry configured to control the DDS circuitry to implement a first delay in ultrasound data from the first ADC and a second delay in ultrasound data from the second ADC.

In some embodiments, the first delay corrects for the first timing delay and the second delay corrects for the second timing delay. In some embodiments, an amount of the first delay is substantially equal to an amount of time represented by the first timing delay and in an opposite time direction and an amount of the second delay is substantially equal to an amount of time represented by the second timing delay and in an opposite time direction. In some embodiments, the first delay includes a delay for correcting for the first timing delay and a delay for beamforming the ultrasound data from the first ADC and the second delay includes a delay for correcting for the second timing delay and a delay for beamforming the ultrasound data from the second ADC. In some embodiments, the first timing delay represents a delay forward in time and the first delay is backward in time or the first timing delay represents a delay backward in time and the first delay is forward in time.

In some embodiments, the ultrasound device further includes beamforming circuitry configured to implement a first delay in ultrasound data from the first ADC and a second delay in ultrasound data from the second ADC, where the first delay and the second delay are different. In some embodiments, the first delay includes a delay for correcting for the first timing delay and a delay for beam-forming the ultrasound data from the first ADC and the second delay includes a delay for correcting for the second timing delay and a delay for beamforming the ultrasound data from the second ADC. In some embodiments, interpo-lation filters, linear interpolation, or fractional delay filters are used to correct for the first timing delay and the second timing delay.

In some embodiments, the first ADC and the second ADC are configured to operate simultaneously using the first ADC clock signal and the second ADC clock signal, respectively. In some embodiments, the first ADC clock signal and the second ADC clock signal are strobe signals. In some embodiments, the ultrasound device comprises an ultra-sound-on-chip. In some embodiments the ultrasound-on-chip includes the first ADC and the second ADC and a plurality of ultrasonic transducers. In some embodiments, the first ADC, the second ADC, and a plurality of ultrasonic transducers are incorporated together on an integrated circuit chip or one or more integrated circuit chips packaged together. In some embodiments, the ultrasound device comprises an ultrasound-on-chip including hundreds of ADCs, thousands of ADCs, or tens of thousands of ADCs.

Some aspects include a method to perform the actions that the ultrasound device is configured to perform.

BRIEF DESCRIPTION OF THE DRAWINGS

Various aspects and embodiments will be described with reference to the following exemplary and non-limiting figures. It should be appreciated that the figures are not necessarily drawn to scale. Items appearing in multiple figures are indicated by the same or a similar reference number in all the figures in which they appear.

FIG. 5 illustrates an example process for processing ultrasound data in an ultrasound system, in accordance with certain embodiments described herein;

DETAILED DESCRIPTION

Figure 1:
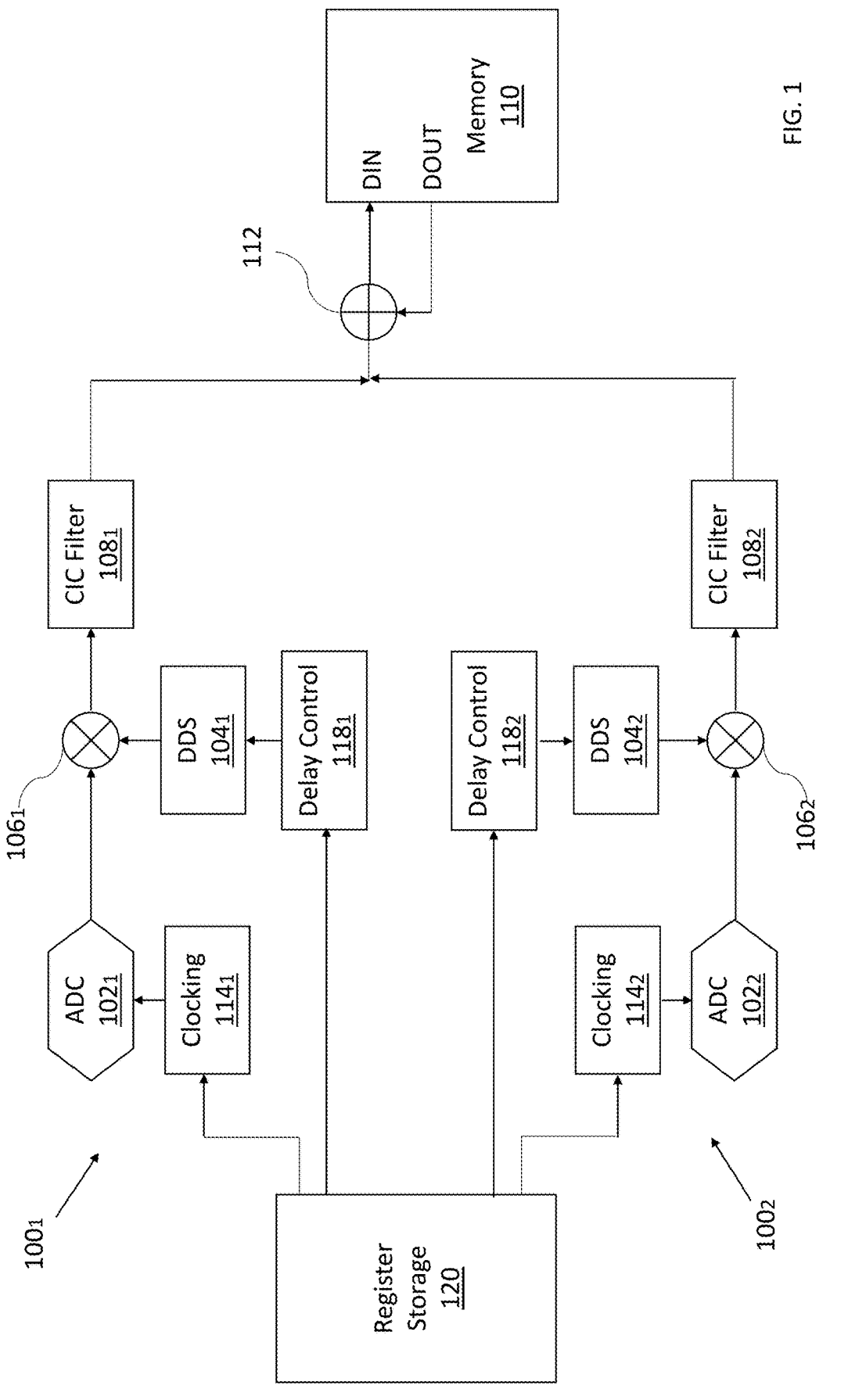
FIG. 1 illustrates an example datapath for ultrasound data received by an ultrasound device, in accordance with certain embodiments described herein.

Recent advances in ultrasound technology have enabled large arrays of ultrasonic transducers and ultrasound processing units (UPUs) to be incorporated onto an integrated circuit to form an ultrasound-on-chip. Each UPU may include, for example, high-voltage pulsers to drive the ultrasonic transducers to emit ultrasound waves; analog and mixed-signal receiver channels to receive and digitize ultrasound echoes; digital processing circuitry to filter, compress, and/or beamform the digital data from each channel; and digital sequencing circuitry to control and synchronize different parts of the UPU circuitry. The ultrasound-on-chip may include one integrated circuit chip or multiple integrated circuit chips packaged together, with various portions of UPU circuitry allocated between the different integrated circuit chips. An ultrasound-on-chip can form the core of a handheld ultrasound probe or an ultrasound device having another form factor. For further description of ultrasound-on-chips, see U.S. patent application Ser. No. 15/626,711 titled "UNIVERSAL ULTRASOUND DEVICE AND RELATED APPARATUS AND METHODS," filed on Jun. 19, 2017 and published as U.S. Pat. App. Publication No. 2017-0360399 A1 (and assigned to the assignee of the instant application), which is incorporated by reference herein in its entirety.

Certain ultrasound devices, such as those including an ultrasound-on-chip, may have on the order of hundreds, thousands, or tens of thousands of analog-to-digital converters (ADCs). In some cases, if the digital switching activity of a large number of ADCs in an ultrasound device occurs simultaneously, this may cause significant draw in current from the power supply, power supply noise, and/or transfer of digital switching activity through capacitive coupling to nearby low bandwidth and/or low amplitude analog signals. This can, in turn, cause noise in images and measurements generated based on the analog signals. The inventors have recognized that ADC clock signals having different timing delays (where a delay may be backward or forward in time) may be provided to different ADCs. For example, different ADC clock signals may control the timing of the different ADCs so that the sample and hold operations of different ADCs start at times that are different by a fraction of a sampling clock period. This may cause the simultaneous digital switching activity of the ADCs to be reduced, and this may reduce noise in images and measurements generated based on the analog signals. The inventors have also recognized that it may be helpful to correct for the timing delays of the ADC clock signals, because otherwise, beamforming delays implemented for the ultrasound data from the ADCs may be inaccurate. In some embodiments, delay control circuitry controlling direct digital synthesis (DDS) circuitry to implement delays in ultrasound data from ADCs may be used to correct for the timing delays. For example, if an ADC clock signal has a timing delay representing a delay of $\tau$ forward in time, then the delay control circuitry may control the DDS circuitry to implement a delay of $\tau$ (or substantially equal to $\tau$) backward in time. As another example, if the ADC clock signal has a timing delay representing a delay of $\tau$ backward in time, then the delay control circuitry may control the DDS circuitry to implement a delay of $\tau$ (or substantially equal to $\tau$) forward in time. In some embodiments, the delay control circuitry may control the DDS circuitry to implement a delay both for correcting for the ADC clock signal timing delay and for beamforming the ultrasound data from the ADCs. In other words, the delay implemented may be the sum of the delay for correcting for the ADC clock signal and the delay for beamforming. In some embodiments, rather than or in addition to correcting for ADC clock signal timing delays with delay control circuitry controlling DDS circuitry, beamforming delays used in downstream beamforming circuitry and/or software may correct for the ADC clock signal timing delays. In other words, a delay implemented by the beamforming circuitry and/or software may be the sum of the delay for correcting for the ADC clock signal and the delay for beamforming.

It should be appreciated that the embodiments described herein may be implemented in any of numerous ways. Examples of specific implementations are provided below for illustrative purposes only. It should be appreciated that these embodiments and the features/capabilities provided may be used individually, all together, or in any combination of two or more, as aspects of the technology described herein are not limited in this respect.

FIG. 1 illustrates example receive circuitry in an ultrasound device, in accordance with certain embodiments described herein. The receive circuitry includes a datapath $100_1$, a datapath $100_2$, and register storage 120. The datapath $100_1$ includes an analog-to-digital converter (ADC) $102_1$, direct digital synthesis (DDS) circuitry $104_1$, a multiplier $106_1$, a cascaded integrator-comb (CIC) filter $108_1$, memory 110, an adder 112, clocking circuitry $114_1$, and delay control circuitry $118_1$. The datapath $100_2$ includes an ADC $102_2$, DDS circuitry $104_2$, a multiplier $106_2$, a CIC filter $108_2$, the memory 110, the adder 112, clocking circuitry $114_2$, and delay control circuitry $118_2$. All the receive circuitry illustrated in FIG. 1 may be in an ultrasound-on-chip device in a handheld ultrasound probe, or another type of ultrasound device such as a patch or pill.

The output of the ADC $102_1$ is coupled to one input of the multiplier $106_1$. The output of the DDS circuitry $104_1$ is coupled to a second input of the multiplier $106_1$. The output of the multiplier $106_1$ is coupled to the input of the CIC filter $108_1$. The clocking circuitry $114_1$ is coupled to the ADC $102_1$. The delay control circuitry $118_1$ is coupled to the DDS circuitry $104_1$. The output of the CIC filter $108_1$ is coupled to a first input of the adder 112. The output of the adder 112 is coupled to a data-in (DIN) terminal of the memory 110. The output of the ADC $102_2$ is coupled to one input of the multiplier $106_2$. The output of the DDS circuitry $104_2$ is coupled to a second input of the multiplier $106_2$. The output of the multiplier $106_2$ is coupled to the input of the CIC filter $108_2$. The clocking circuitry $114_2$ is coupled to the ADC $102_2$. The delay control circuitry $118_2$ is coupled to the DDS circuitry $104_2$. The output of the CIC filter $108_2$ is coupled to the first input of the adder 112. The output of the adder 112 is coupled to a data-in (DIN) terminal of the memory 110. A data-out (DOUT) terminal of the memory 110 is coupled to a second input of the adder 112. The register storage circuitry 120 is coupled to the clocking circuitry $114_1$, the clocking circuitry $114_2$, the delay control circuitry $118_1$, and the delay control circuitry $118_2$.

The ADC $102_1$ and the ADC $102_2$ may be configured to convert analog ultrasound data to digital ultrasound data. The ADC $102_1$ may be coupled to a first set of ultrasonic transducers (where a set may include one more) and configured to convert analog ultrasound data from that first set of ultrasound transducers to digital ultrasound data. The ADC $102_2$ may be coupled to a second set of ultrasonic transducers and configured to convert analog ultrasound data from that second set of ultrasound transducers to digital ultrasound data. In some embodiments, the first and second sets of ultrasonic transducers may be in different azimuthal channels but the same elevational channel. In some embodiments, the first and second sets of ultrasonic transducers may be in different elevational channels but the same azimuthal channel. In some embodiments, the first and second sets of ultrasonic transducers may be in different elevational and azimuthal channels. In some embodiments, the first and second sets of ultrasonic transducers may be in the same elevational and azimuthal channels. In some embodiments, the ADC $102_1$ may be in one ultrasound processing unit (UPU) and the ADC $102_2$ may be in another UPU. Each UPU may be a self-contained ultrasound processing unit that forms a sub-array of a complete ultrasound imaging array in a scalable fashion. Each UPU may include, for example, high-voltage pulsers to drive ultrasonic transducers to emit ultrasound; analog and mixed-signal receiver channels to receive and digitize ultrasound echoes; digital processing circuitry to filter, compress, and/or beamform the digital data from each channel; and digital sequencing circuitry to control and coordinate different parts of the circuitry to work in synchronization with one another. In some embodiments, the ADC $102_1$ and the ADC $102_2$ may be in the same UPU.

The clocking circuitry $114_1$ may be configured to provide an ADC clock signal (e.g., a strobe signal) to the ADC $102_1$. The clocking circuitry $114_2$ may be configured to provide an ADC clock signal (e.g., a strobe signal) to the ADC $102_2$. In some embodiments, the ADC clock signals may both be derived, for example by the clocking circuitry $114_1$ and $114_2$, from a system clock having a frequency $f_{clk}$ such that the ADC clock signals both have a frequency of $f_{clk}/R$. In some embodiments, R may be equal to or any integer between 4 or 31. For any given R, there may be R different choices for the timing delay of the ADC clock signals. When different ADCs have ADC clock signals with different timing delays, this may mean that the different ADC clock signals control the timing of the different ADCs so that the sample and hold operations of different ADCs start at times that are different by a fraction of a sampling clock period. Timing delays may be measured in units of degrees. The timing delay options may be referred to as option $0, 1, 2 \ldots R-1$, where the timing delay for each option is $0, 360/R, 2*360/R \ldots (R-1)*360/R$ degrees. The clocking circuitry $114_1$ may provide an ADC clock signal having one of the timing delay options to the ADC $102_1$, and the clocking circuitry $114_2$ may provide an ADC clock signal having a different one of the timing delay options to the ADC $102_2$. The ADC $102_1$ and the ADC $102_2$ may operate simultaneously each using an ADC clock signal having the same frequency but a different timing delay.

The above description has described that the clocking circuitry $114_1$ and the clocking circuitry $114_2$ may derive the ADC clock signals from a system clock having a frequency $f_{clk}$ such that the ADC clock signals have different timing delays and both have a frequency of $f_{clk}/R$. In other words, the ADC clock signals may be lower in frequency than the system clock. However, the clocking circuitry $114_1$ and the clocking circuitry $114_2$ may generate ADC clock signals having different timing delays using other methods, such as by using phase-locked loop (PLL) circuitry. Using PLL circuitry may not require deriving the ADC clock signals from a higher-frequency signal.

In some embodiments, the datapath $100_1$ may be one of multiple datapaths in one ultrasound processing unit (UPU), and the datapath $100_2$ may be one of multiple datapaths in one UPU. In some embodiments, the datapath $100_1$ may each be one of multiple datapaths in a single UPU. In some embodiments, each ADC in a given UPU may receive an ADC clock signal having one timing delay, while each ADC in another UPU may receive an ADC clock signal having another timing delay. For example, the ADC $102_1$ and the ADC $102_2$ may be in different UPUs. In some embodiments, certain ADCs (one or more) in a given UPU may receive an ADC clock signal having one timing delay and other ADCs in the UPU may receive an ADC clock signal having a different timing delay. For example, the ADC $102_1$ and the ADC $102_2$ may be in the same UPU.

While FIG. 1 illustrates two ADCs with two different timing delays, it should be appreciated that more than two ADCs may each have different timing delays. For example, there may be M timing delay options, where each of N (N>=M) is assigned one of the M timing delay options. Thus, different timing delays may be assigned to different modules, where as examples, a module may be an individual ADC among multiple ADCs within an UPU, or a module may be an UPU among multiple UPUs. In some embodiments, timing delays may be assigned to modules according to a sawtooth pattern. Each module may have an index N (e.g., based on spatial location), and a given module N may receive an ADC clock signal having the timing delay N mod R, or (N mode R)/R*360 degrees, where each ADC clock signal is derived from a system clock having a frequency $f_{clk}$ such that each ADC clock signal has a frequency of $f_{clk}$/R and there may be R different choices for the timing delay. For example, if R=5, modules 10, 11, 12, 13, 14 may have timing delays 0, 1, 2, 3, 4, which may correspond to 0, 72, 144, 216, 288 degrees. As another example, if R=4, modules 8, 9, 10, 11 may have timing delays 0, 1, 2, 3, which may correspond to 0, 90, 180, 270 degrees. In some embodiments, timing delays may be assigned randomly to modules. In some embodiments, each module may have an index N (e.g., based on spatial location), and modules having an even N may receive a first ADC clock signal and modules having an odd N may receive a second ADC clock signal offset 180 degrees from the first ADC clock signal (but having the same frequency). In other words, for each group of 2 modules, the modules may receive timing delays 0 and 180 degrees. In some embodiments, for each group of 4 modules, the modules may receive timing delays (listed in order of spatial location) of 0, 0, 180, and 180 degrees. In some embodiments, for each group of 8 modules, the modules may receive timing delays (listed in order of spatial location) of 0, 0, 0, 0, 180, 180, 180, and 180 degrees.

In the example of just 2 different timing delays. for a given set of modules, the timing delays for the modules listed in order of spatial location may be 0, 0, 0 . . . 0, 0, 180, 180, 180 . . . 180, 180 in some embodiments or 0, 180, 0, 180 . . . 0, 180, 0, 180. Generally, in some embodiments, a given timing delay may be assigned to spatially adjacent modules, or adjacent modules may receive different timing delays. In some embodiments, assigning a given timing delay to spatially adjacent modules may be helpful when data from spatially adjacent modules is summed (e.g., for azimuthal summing).

In some embodiments, assigning one of two timing delays (e.g., 0 or 180 degrees) to each module may reduce noise to an acceptable degree when the ADC clock signals have a frequency above a certain threshold (e.g., 20 megasamples/second). In some embodiments, using a sawtooth pattern to assign one of three or more timing delays to each module may reduce noise to an acceptable degree when the ADC clock signals have a frequency below the threshold (e.g., 20 megasamples/second).

As one non-limiting example, when an ultrasound-on-chip device comprises on the order of a thousand ADCs and 4 different timing delays are assigned to different UPUs, the correlation noise may be reduced by 6 dB in the range of 0-12.5 MHz and by 10 dB in the range of 2-4 MHz compared to a scenario in which all of the ADCs receive clocking signals that do not have different timing delays.

As described above, in some cases, if the digital switching activity of a larger number of ADCs in an ultrasound device occurs simultaneously, this may cause significant draw in current from the power supply, power supply noise, and/or transfer of digital switching activity through capacitive coupling to nearby low bandwidth and/or low amplitude analog signals. This can, in turn, cause noise in images and measurements generated based on the analog signals. By providing ADC clock signals having different timing delays to different ADCs (e.g., the ADC 102₁ and the ADC 102₂), the simultaneous digital switching activity of the ADCs may be reduced, and this may reduce noise in images and measurements generated based on the analog signals.

The DDS circuitry 104₁ may be configured to translate the frequency of the ultrasound data from the ADC 102₁ (after it has been digitized). For example, if the ultrasound data from the ADC 102₁ occupies a certain band of frequencies, the DDS circuitry 104 may be configured to modulate the ultrasound data from the ADC 102₁ such that it occupies a different band of frequencies, for example a band of frequencies with a lower center frequency. The DDS circuitry 104₁ may be configured to generate digital sinusoidal waveforms for forming a complex signal $e^{-i\omega_{DDS}t}$ where $\omega_{DDS}=2\pi f_{DDS}$ is the center frequency of interest. To generate these digital sinusoidal waveforms, the DDS circuitry 104₁ may include a DDS phase counter. The value of the DDS phase counter may be used in sine and/or cosine lookup circuits to generate the sine and cosine portions of the complex signal $e^{-i\omega_{DDS}t}$. The increment value of the DDS phase counter may be proportional to $1/\omega_{DDS}$. The DDS circuitry 104₂ may be configured to operate in the same manner on ultrasound data from the ADC 102₂.

The multiplier 106₁ may be configured to multiply the ultrasound data from the ADC 102₁ (after it has been digitized) with the complex signal $e^{-i\omega_{DDS}t}$ using the sinusoidal waveforms generated by the DDS circuitry 104₁. In particular, to realize this multiplication, the multiplier 106 may use quadrature modulation. The multiplier 106₂ may be configured to operate in the same manner on ultrasound data from the ADC 102₂ and sinusoidal waveforms generated by the DDS circuitry 104₂.

The delay control circuitry 118₁ may be configured to control the DDS circuitry 104₁ to add a delay (where, as referred to herein, a delay may be either forward or backward in time, unless specified otherwise) to the complex signal generated by the DDS circuitry 104₁ for multiplying with ultrasound data. For narrow band signals or small delays $\tau$, $f(t-\tau) \approx e^{-i\omega\tau}f(t)$. In other words, a delay $\tau$ of a signal f(t) may be implemented by multiplying f(t) by $e^{-i\omega\tau}$. As described above, the DDS circuitry 104₁ and the multiplier 106₁ may be already configured to multiply the ultrasound data by $e^{-i\omega_{DDS}t}$. The delay control circuitry 118₁ may be configured to implement a delay by adding an offset to the waveform used for multiplication, so that the ultrasound data is instead multiplied by $e^{-i\omega_{DDS}(t-\tau)}$. The delay control circuitry 118₂ may be configured to operate in the same manner on the DDS circuitry 104₂, such that the delay implemented by the DDS circuitry 104₂ is different from the delay implemented by the DDS circuitry 104₁. Thus, the delay control circuitry 118₁ and 118₂ may control the DDS circuitry 104₁ and the DDS circuitry 104₂, respectively, to implement different delays such that ultrasound data from the ADC 102₁ is be multiplied by $e^{-i\omega_{DDS}(t-\tau1)}$ while ultrasound data from the ADC 102₂ is multiplied by $e^{-i\omega_{DDS}(t-\tau2)}$.

As described above, the clocking circuitry 114₁ may provide an ADC clock signal having one timing delay to the ADC 102₁, and the clocking circuitry 114₂ may provide an ADC clock signal having a different timing delay to the ADC 102₂. In some embodiments, the delay control circuitry 118₁ may control the DDS circuitry 104₁ to implement a delay to correct for the timing delay of the ADC clock signal received by the ADC 102₁ and the delay control circuitry 118₂ may control the DDS circuitry 104₂ to implement a delay to correct for the timing delay of the ADC clock signal received by the ADC 102₂. For example, if the ADC clock signal has a timing delay representing a delay of $\tau$ forward in time, then the delay control circuitry 118₁ may control the DDS circuitry 104₁ to implement a delay of $\tau$ (or substantially equal to $\tau$) backward in time. As another example, if the ADC clock signal has a timing delay representing a delay of $\tau$ backward in time, then the delay control circuitry $118_1$ may control the DDS circuitry $104_1$ to implement a delay of $\tau$ (or substantially equal to $\tau$) forward in time. In other words, the delay implemented by the DDS circuitry may be substantially equal to an amount of time represented by the timing delay of the ADC clock signal, but in the opposite time direction. The delay implemented by the DDS circuitry may therefore substantially cancel the timing delay of the ADC clock signal.

In some embodiments, it may be helpful to correct for the timing delay of the ADC clock signal received by the ADC $102_1$ and the timing delay of the ADC clock signal received by the ADC $102_2$, because otherwise, beamforming delays implemented for the ultrasound data from the ADC $102_1$ and the ADC $102_2$ may be inaccurate. During beamforming, ultrasound data that starts at an initial time $t=t_0$ may be delayed to some other time before being summed with other ultrasound data. Due to the ADC clock signal offset, without correction, then the first sample from an ADC may not be at $t=t_0$ but at $t=R/f_{clk}$ for some R.

In some embodiments, the delay control circuitry $118_1$ and/or $118_2$ may control the DDS circuitry $104_1$ and $104_2$, respectively, to implement a delay both for correcting for the ADC clock signal timing delay and for beamforming the ultrasound data from the ADCs $102_1$ and $102_2$. In other words, the delay implemented may be the sum of the delay for correcting for the ADC clock signal and the delay for beamforming. In some embodiments, it may be helpful to choose whether the timing delay of the ADC clock signal is forward or backward in time, and correspondingly choose whether the delay implemented by delay control circuitry and DDS circuitry is backward or forward in time, such that the total delay implemented by the delay control circuitry and DDS circuitry (e.g., the sum of the delays for correcting for the ADC clock signal timing delay and for beamforming), whether forward or backward in time, is as close to 0 modulo $2\pi$ as possible. This may be helpful because the delay implemented by the delay control circuitry and DDS circuitry may only be an approximate delay, and the quality of that approximation may decrease as the delay gets larger. In some embodiments, the delay control circuitry $118_1$ and/or $118_2$ may not control the DDS circuitry $104_1$ and/or $104_2$ to implement any delay for beamforming.

The register storage circuitry 120 may have a register that stores a timing delay value for each of the clocking circuitry $114_1$ and the clocking circuitry $114_2$. Each of the clocking circuitry $114_1$ and the clocking circuitry $114_2$ may be configured to retrieve the corresponding timing delay value from the register storage circuitry 120 for providing ADC clock signals to the ADC $102_1$ and ADC $102_2$, respectively, having those timing delay values. The register storage circuitry 120 may also have a register that stores a delay value for each of the delay control circuitry $118_1$ and the delay control circuitry $118_2$. Each of the delay control circuitry $118_1$ and the delay control circuitry $118_2$ may be configured to retrieve the corresponding delay value from the register storage circuitry 120 for controlling the DDS circuitry $104_1$ and $104_2$, respectively, to implement delays having those delay values. In some embodiments, each of the delay control circuitry $118_1$ and the delay control circuitry $118_2$ may be configured to provide the value to a DDS phase counter of the DDS circuitry $104_1$ and the DDS circuitry $104_2$, respectively. The minimum offset resolution provided by the delay control circuitry $118_1$ and the delay control circuitry $118_2$ may be limited by the resolution $B_{DDS}$ of the DDS phase counters such that the minimum offset resolution is $1/(f_{DDS}B_{DDS})$. The minimum offset resolution and the dynamic range should be sufficient to correct for timing delays of the ADC clock signal.

The CIC filter $108_1$ may be configured to filter ultrasound data after it has been modulated by the DDS circuitry $104_1$ and the multiplier $106_1$. In some embodiments, the CIC filter $108_1$ may be configured as a low-pass filter to remove high frequency images of the ultrasound data. The CIC filter $108_1$ may be configured to operate in the same manner on ultrasound data after it has been modulated by the DDS circuitry $104_2$ and the multiplier $106_2$.

The memory 110 may be configured to store the ultrasound data (after it has been filtered). In some embodiments, the memory 110 may be configured as a static random-access memory (SRAM), although other types of memory may be used. The memory 110 may be configured to output, at the DOUT terminal, data stored in the memory 110 at an address that is provided at an ADDR terminal (not shown in figure). The memory 110 may be configured to write to the memory 110, at the address that is provided at the address terminal, the data inputted at the DIN terminal.

The adder 112 may be configured to add the ultrasound data (after it has been filtered) to data at the DOUT output of the memory 110 that has been retrieved from a particular address (based on the address terminal) of the memory 110 and provide the sum at the DIN input of the memory 110 to be written to the same address of the memory 110. Thus, the adder 112 and memory 110 may be configured as accumulation circuitry. While the output of the CIC filter $108_1$ and the CIC filter $108_2$ are illustrated as being directly coupled to an input on the adder 112, in some embodiments these outputs may actually be multiplexed to the adder 112 such that one output can be written to the memory 110 and then the other output can be written to the memory 110.

Figure 2:
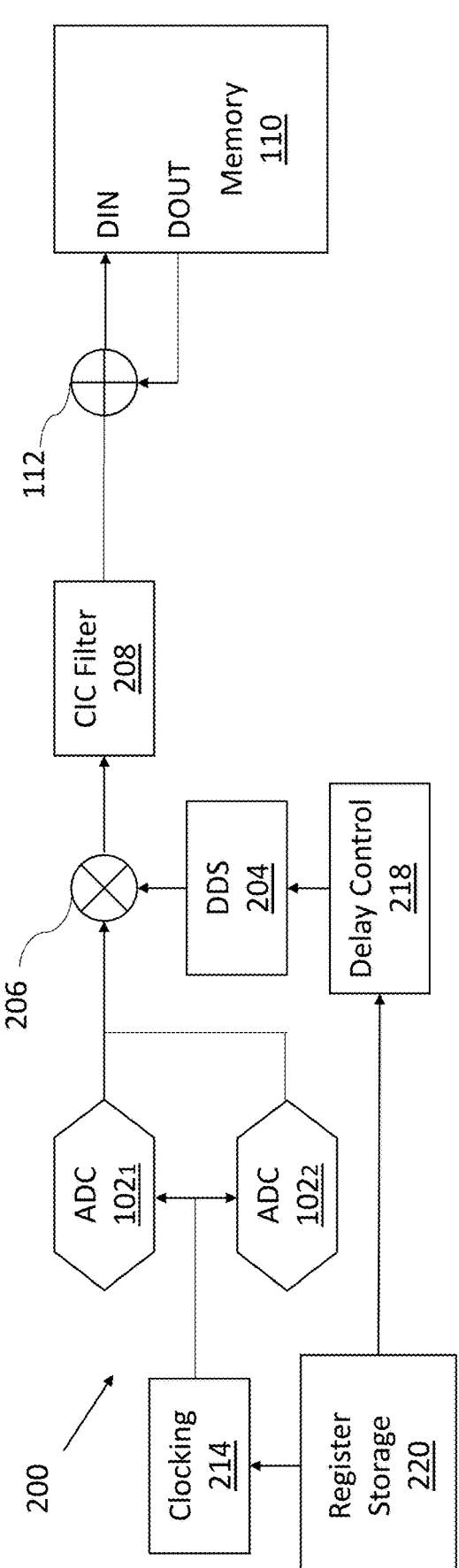
FIG. 2 illustrates another example datapath for ultrasound data received by an ultrasound device, in accordance with certain embodiments described herein.

FIG. 2 illustrates example receive circuitry in an ultrasound device, in accordance with certain embodiments described herein. The receive circuitry includes a datapath 200 and register storage 220. The datapath 200 includes the ADC $102_1$, the ADC $102_2$, DDS circuitry 204, a multiplier 206, a CIC filter 208, the memory 110, the adder 112, clocking circuitry 214, and delay control circuitry 218. All the receive circuitry illustrated in FIG. 2 may be in an ultrasound-on-chip device in a handheld ultrasound probe, or another type of ultrasound device such as a patch or pill.

The ADC $101_1$ and the ADC $101_2$ share circuitry in the datapath 200. The outputs of the ADC $102_1$ and the ADC $102_2$ are coupled (e.g., through multiplexers not illustrated in the figure) to one input of the multiplier 206. The output of the DDS circuitry 204 is coupled to a second input of the multiplier 206. The output of the multiplier 206 is coupled to the input of the CIC filter 208. The clocking circuitry 214 is coupled to the ADC $102_1$ and the ADC $102_2$. The delay control circuitry 218 is coupled to the DDS circuitry 204. The output of the CIC filter 208 is coupled to a first input of the adder 112. The output of the adder 112 is coupled to a data-in (DIN) terminal of the memory 110. The register storage circuitry 220 is coupled to the clocking circuitry 214 and the delay control circuitry 218. Further description of operation of the ADC $102_1$, the ADC $102_2$, the DDS circuitry 204, the CIC filter 208, the adder 112, and the memory 110, may be found with reference to the description of the ADC $102_1$, the ADC $102_2$, the DDS circuitry 2041 and $104_2$, the CIC filter $108_1$ and $108_2$, the adder 112, and the memory 110 of FIG. 1.

As illustrated, the ADCs $102_1$ and $102_2$ share a single multiplier 206 and CIC filter 208. The multiplier 206 and CIC filter 208 may be clocked at four times the ADC conversion frequency. This is because the multiplication step may be preceded by transformation of the real valued signal from an ADC into "in phase" (real) and "out of phase" (complex) parts. Thus, the output of the two ADCs $102_1$ and $102_2$ may result in two real and two imaginary signals, for a total of 4 signals that are processed at four times the ADC conversion frequency. Each of these signals may then pipeline into the multiplication stage of the multiplier 206 and then into the CIC filter 208.

The clocking circuitry 214 may be configured to provide ADC clock signals (e.g., strobe signals) to the ADC $102_1$ and the ADC $102_2$. In some embodiments, the ADC clock signals may be derived, for example by the clocking circuitry 214, from a system clock having a frequency $f_{clk}$ such that the ADC clock signals have a frequency of $f_{clk}$/R. In some embodiments, R may be equal to or any integer between 4 or 31. For any given R, there may be R different choices for the timing delay of the ADC clock signals. When different ADCs have ADC clock signals with different timing delays, this may mean that the different ADC clock signals control the timing of the different ADCs so that the sample and hold operations of different ADCs start at times that are different by a fraction of a sampling clock period. Timing delays may be measured in units of degrees. The timing delay options may be referred to as option 0, 1, 2 . . . R–1, where the timing delay for each option is 0, 360/R, 2*360/R . . . (R–1)*360/R degrees. The clocking circuitry 214 may provide an ADC clock signal having one of the timing delay options to the ADC $102_1$, and the clocking circuitry 214 may provide an ADC clock signal having a different one of the timing delay options to the ADC $102_2$. The ADC $102_1$ and the ADC $102_2$ may operate simultaneously each using an ADC clock signal having the same frequency but a different timing delay. The above description of various options for assigning different timing delays to different modules (e.g., on the level of individual ADCs or on the level of UPUs) applies to the embodiment of FIG. 2, as well as the embodiments of FIGS. 3-4.

The above description has described that the clocking circuitry 214 may derive the ADC clock signals from a system clock having a frequency $f_{clk}$ such that the ADC clock signals have different timing delays and both have a frequency of $f_{clk}$/R. In other words, the ADC clock signals may be lower in frequency than the system clock. However, the clocking circuitry 214 may generate ADC clock signals having different timing delays using other methods, such as by using phase-locked loop (PLL) circuitry. Using PLL circuitry may not require deriving the ADC clock signals from a higher-frequency signal.

The delay control circuitry 218 may be configured to control the DDS circuitry 204 to add a different delay to the complex signal generated by the DDS circuitry 204 for multiplying with ultrasound data from different ADCs. For example, one delay may be added to ultrasound data from the ADC $102_1$, and another delay may be added to ultrasound data from the ADC $102_2$. For narrow band signals or small delays $\tau$, $f(t-\tau) \approx e^{-i\omega\tau} f(t)$. In other words, a delay $\tau$ of a signal $f(t)$ may be implemented by multiplying $f(t)$ by $e^{-i\omega\tau}$. The DDS circuitry 204 and the multiplier 106 may be already configured to multiply the ultrasound data by $e^{-i\omega_{DDS}t}$. The delay control circuitry 218 may be configured to implement a delay by adding, for each of the ADCs $102_1$ and $102_2$, a different offset to the waveform used for multiplication, so that the ultrasound data is instead multiplied by $e^{-i\omega_{DDS}(t-\tau)}$. For example, ultrasound data from the ADC $102_1$ may be multiplied by $e^{-i\omega_{DDS}(t-\tau1)}$ while ultrasound data from the ADC $102_2$ may be multiplied by $e^{-i\omega_{DDS}(t-\tau2)}$ For generating digital sinusoidal waveforms for forming complex signals, the DDS circuitry 204 may include a DDS phase counter, the value of which may be used in sine and/or cosine circuits. In some embodiments, the DDS circuitry 204 may include multiple DDS phase counters, for example one for each of the ADCs $102_1$ and $102_2$, and each of the DDS phase counters may be initialized to a different value that, upon being used by the DDS circuitry 204, provides the delay T. When the multiplier 106 is processing data from a specific ADC, the multiplier 106 may multiply the data by a complex signal formed based on waveforms from the DDS circuitry 204 when using that ADC's DDS phase counter. In some embodiments, the DDS circuitry 204 may include a single DDS phase counter and an adder configured to add the DDS phase counter value to a value specific to the ADC the ultrasound data from which is being processed.

As described above, the clocking circuitry 214 may provide an ADC clock signal having one timing delay to the ADC $102_1$, and the clocking circuitry 214 may provide an ADC clock signal having a different one of the timing delay to the ADC $102_2$. In some embodiments, the delay control circuitry 218 may implement a timing delay to correct for the timing delay of the ADC clock signal received by the ADC $102_1$ and the delay control circuitry 218 may implement a timing delay to correct for the timing delay of the ADC clock signal received by the ADC $102_2$. For example, if the ADC clock signal has a timing delay representing a delay of $\tau$ forward in time, then the delay control circuitry 218 may control the DDS circuitry 204 to implement a delay of $\tau$ (or substantially equal to $\tau$) backward in time. As another example, if the ADC clock signal has a timing delay representing a delay of $\tau$ backward in time, then the delay control circuitry 218 may control the DDS circuitry 204 to implement a delay of $\tau$ (or substantially equal to $\tau$) forward in time. In other words, the delay implemented by the DDS circuitry may be substantially equal to an amount of time represented by the timing delay of the ADC clock signal, but in the opposite time direction. The delay implemented by the DDS circuitry may therefore substantially cancel the timing delay of the ADC clock signal.

In some embodiments, the delay control circuitry 218 may implement delays both for correcting for the ADC clock signal timing delay and for beamforming the ultrasound data from the ADCs $102_1$ and $102_2$. In other words, the delay implemented may be the sum of the delay for correcting for the ADC clock signal and the delay for beamforming. In some embodiments, it may be helpful to choose whether the timing delay of the ADC clock signal is forward or backward in time, and correspondingly choose whether the delay implemented by the delay control circuitry 218 and DDS circuitry 204 is backward or forward in time, such that the total delay implemented by the delay control circuitry 218 and the DDS circuitry 204 (e.g., the sum of the delays for correcting for the ADC clock signal timing delay and for beamforming), whether forward or backward in time, is as close to 0 modulo $2\pi$ as possible. This may be helpful because the delay implemented by the delay control circuitry and DDS circuitry may only be an approximate delay, and the quality of that approximation may decrease as the delay gets larger. In some embodiments, the delay control circuitry 218 may not control the DDS circuitry 204 implement any delay for beamforming.

The register storage circuitry 220 may have a register that stores offset values for the clocking circuitry 214. The clocking circuitry 214 may be configured to retrieve values corresponding to each of the ADCs $102_1$ and $102_2$ from the register storage circuitry 220 for providing ADC clock signals to the ADC $102_1$ and ADC $102_2$, respectively, having those timing delay values. The register storage circuitry 220 may also have registers that store delay values for the delay control circuitry 218. The delay control circuitry 218 may be configured to retrieve delay values corresponding to each of the ADCs $102_1$ and $102_2$ from the register storage circuitry 220 for controlling the DDS circuitry 204 respectively, to implement delays having those delay values for ultrasound data from the ADCs $102_1$ and $102_2$, respectively. In some embodiments, the delay control circuitry 218 may be configured to provide the values to DDS phase counters of the DDS circuitry 204 corresponding to each of the ADCs $102_1$. In some embodiments, the delay control circuitry 218 may be configured to provide the values to an adder configured to add the values in turn to the value of a single DDS phase counter of the DDS circuitry 204.

Figure 3:
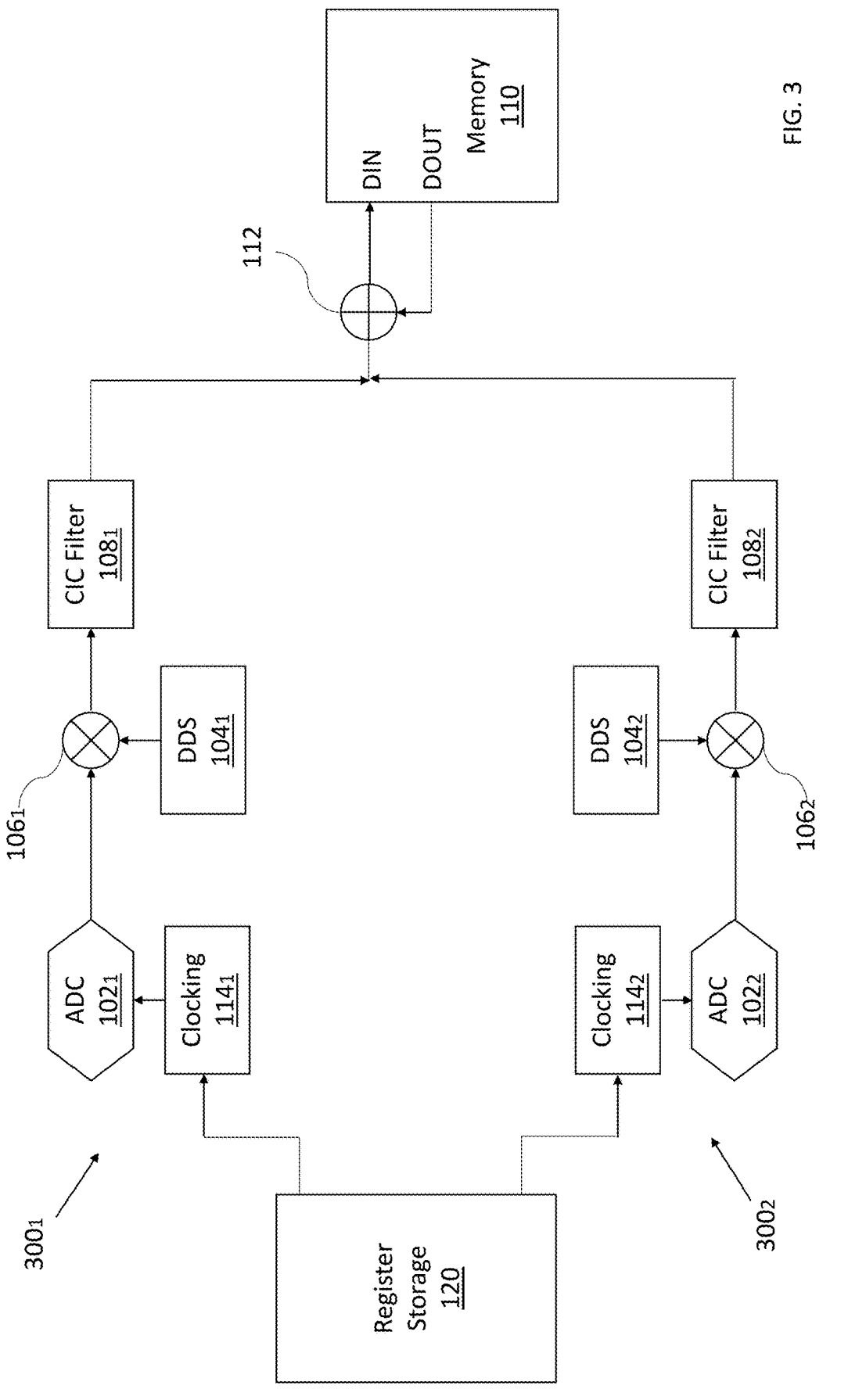
FIG. 3 illustrates another example datapath for ultrasound data received by an ultrasound device, in accordance with certain embodiments described herein.
Figure 4:
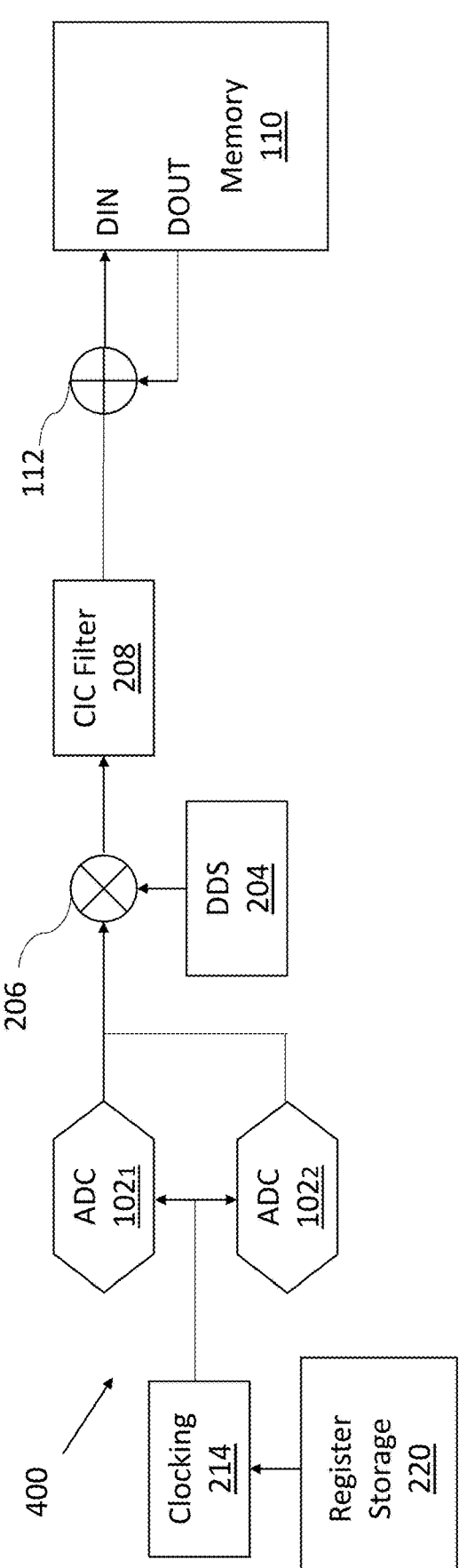
FIG. 4 illustrates another example datapath for ultrasound data received by an ultrasound device, in accordance with certain embodiments described herein.

In some embodiments, datapaths (e.g., the datapaths $100_1$, $100_2$, or 200) may lack control circuitry (e.g., the control circuitry $118_1$, $118_2$, or 218), or the control circuitry may not be configured to control DDS circuitry (e.g., the DDS circuitry $104_1$, $104_2$, or 204) to add a different timing delay to the complex signal generated by the DDS circuitry for multiplying with ultrasound data from the ADC $102_1$ and with ultrasound data from the ADC $102_2$. This may be the case even if clocking circuitry (e.g., the clocking circuitry $114_1$, $114_2$, and/or 214) provides an ADC clock signal having different timing delays to the ADC $102_1$ and to the ADC $102_2$. For high enough ADC clock frequencies and low enough ultrasound wave frequencies, the error that may be introduced in beamforming delays due to the ADC clock signal timing delays may become negligible. In some embodiments, rather than or in addition to correcting for ADC clock signal timing delays with delay control circuitry controlling DDS circuitry, beamforming delays used in downstream beamforming circuitry and/or software may correct for the ADC clock signal timing delays. In other words, a delay implemented by the beamforming circuitry and/or software may be the sum of the delay for correcting for the ADC clock signal and the delay for beamforming. In some embodiments, interpolation filters, linear interpolation, or fractional delay filters may be used to correct for the ADC clock signal timing delays. FIG. 3 illustrates example receive circuitry in an ultrasound device, in accordance with certain embodiments described herein. FIG. 3 illustrates datapaths $300_1$ and $300_2$ which are the same as the datapaths $100_1$ and $100_2$ except that the datapaths $300_1$ and $300_2$ lack the delay control circuitry $118_1$ and $118_2$, respectively. FIG. 4 illustrates example receive circuitry in an ultrasound device, in accordance with certain embodiments described herein. FIG. 4 illustrates a datapath 400 which is the same as the datapath 200 except that the datapath 400 lacks the delay control circuitry 218.

FIG. 5 illustrates an example process 500 for processing ultrasound data in an ultrasound system, in accordance with certain embodiments described herein. The process 500 may be performed by the ultrasound system.

In act 502, the ultrasound device operates a first ADC (e.g., the ADC $102_1$), with a first ADC clock signal having a first timing delay and operates a second ADC with a second ADC clock signal having a second timing delay, where the first and second timing delays are different. In some embodiments, the first ADC may be in one UPU and the second ADC may be in another UPU. In some embodiments, the first ADC and the second ADC may be in the same UPU. In some embodiments, clocking circuitry (e.g., the clocking circuitry $114_1$ or 214) may provide the first ADC clock signal (e.g., a strobe signal) to the first ADC and clocking circuitry (e.g., the clocking circuitry $114_2$ or 214) and provide the second ADC clock signal (e.g., a strobe signal) to the second ADC. In some embodiments, the first and second ADC clock signals may both be derived, for example by the clocking circuitry, from a system clock having a frequency $f_{clk}$ such that the ADC clock signals both have a frequency of $f_{clk}/R$. In some embodiments, R may be equal to or any integer between 4 or 31. For any given R, there may be R different choices for the timing delay of the first and second ADC clock signals. Alternatively, rather than deriving lower-frequency ADC clock signals from a higher-frequency system clock, the clocking circuitry may generate the first and second ADC clock signals having different timing delays using other methods, such as by using phase-locked loop (PLL) circuitry. Using PLL circuitry may not require deriving the first and second ADC clock signals from a higher-frequency signal.

When different ADCs have ADC clock signals with different timing delays, this may mean that the different ADC clock signals control the timing of the different ADCs so that the sample and hold operations of different ADCs start at times that are different by a fraction of a sampling clock period. The first ADC clock signal may have one of the timing delay options and the second ADC clock signal may have a different one of the timing delay options. The first and second ADC clock signals may have the same frequency. The first ADC and the second ADC may operate simultaneously using the first and second ADC clock signals, respectively. The process 500 proceeds from act 502 to act 504.

In act 504, the ultrasound device delays ultrasound data from the first ADC with a delay that corrects (at least approximately) for the first timing delay, and delays ultrasound data from the second ADC with a delay that corrects (at least approximately) for the second timing delay. In some embodiments, delay control circuitry (e.g., the delay control circuitry $118_1$, $118_2$, or 218) may control DDS circuitry (e.g., the DDS circuitry $104_1$, $104_2$, or 204) to add a different delay to the complex signal generated by the DDS circuitry for multiplying with the ultrasound data from the first ADC and the ultrasound data from the second ADC. For example, if the ADC clock signal has a timing delay representing a delay of τ forward in time, then the delay control circuitry may control the DDS circuitry $104_1$ to implement a delay of τ (or substantially equal to τ) backward in time. As another example, if the ADC clock signal has a timing delay representing a delay of τ backward in time, then the delay control circuitry may control the DDS circuitry $104_1$ to implement a delay of τ (or substantially equal to τ) forward in time. In other words, the delay implemented by the DDS circuitry may be substantially equal to an amount of time represented by the timing delay of the ADC clock signal, but in the opposite time direction. The delay implemented by the DDS circuitry may therefore substantially cancel the timing delay of the ADC clock signal.

In some embodiments, the delay control circuitry may implement delays both for correcting for the first and second timing delays and for beamforming the ultrasound data from the first ADC and the ultrasound data from the second ADC. In other words, the delay implemented for each of the first ADC and second ADC may be the sum of the delay for correcting for the respective ADC clock signal and the delay for beamforming. In some embodiments, rather than (or in addition to) correcting for ADC clock signal timing delays with delay control circuitry controlling DDS circuitry, beamforming delays used in downstream beamforming circuitry and/or software may correct for the first and second timing delays. In other words, the delay implemented by the beamforming circuitry and/or software may be the sum of the delay for correcting for the respective ADC clock signal timing delay and the delay for beamforming. In some embodiments, interpolation filters, linear interpolation, or fractional delay filters may be used to correct for the ADC clock signal timing delays. In some embodiments, act 504 may be absent. For high enough ADC clock frequencies and low enough ultrasound wave frequencies, the error that may be introduced in beamforming delays due to the ADC clock signal timing delays may become negligible.

Figure 6:
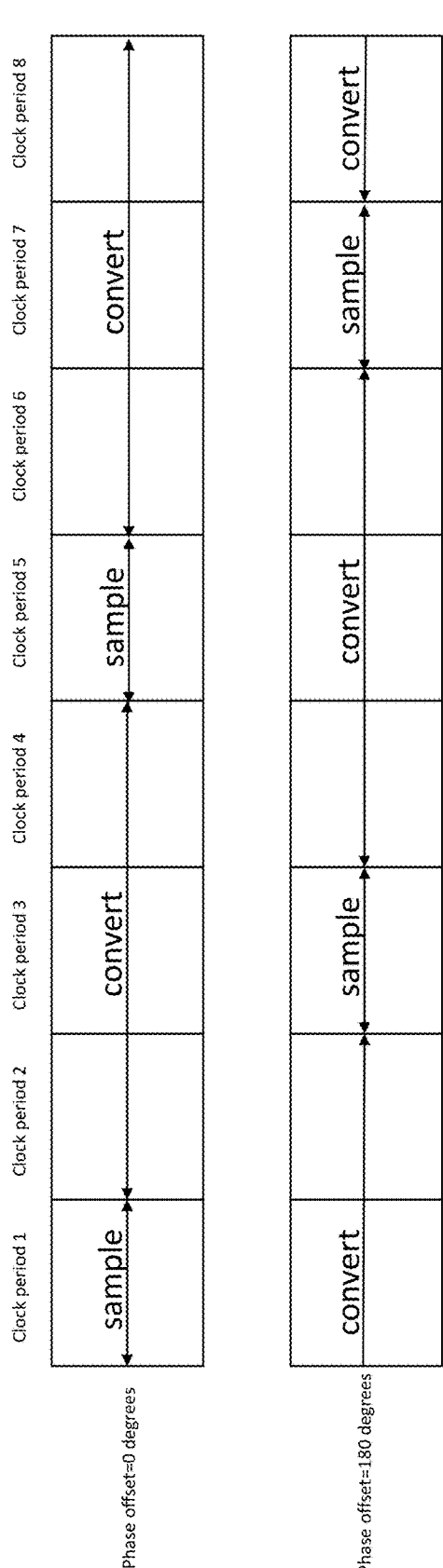
FIG. 6 illustrates an example timing diagram for two ADCs, in accordance with certain embodiments herein.

FIG. 6 illustrates an example timing diagram for two ADCs, in accordance with certain embodiments herein. Eight clock periods are shown, labeled as Clock period 1 . . . Clock period 8. The two ADCs have ADC clock signals having the same frequency, but one ADC clock signal has a timing delay of 0 degrees and the other ADC clock signal has a timing delay of 180 degrees. The two ADCs may be the ADC 102$_1$ and 102$_2$. In FIG. 6, the ADC clock signals have a frequency that is $f_{clk}/4$, where $f_{clk}$ is the frequency of a system clock. Each clock period illustrated in FG. 6 is one clock period of the system clock. As illustrated in FIG. 6, the sampling stage (labeled "sample") for a given ADC occurs during 1 period of the system clock and the conversion stage (labeled "convert") occurs during the following 3 periods of the system clock. The timing sequences for each ADC are offset by 2 clock periods. In general, different ADCs may have ADC clock signals having a frequency that is $f_{clk}/R$, where the sampling stage for a given ADC occurs during 1 period of the system clock and the conversion stage occurs during the following R–1 periods of the system clock. The timing sequences for different ADCs may be offset by 1 to R–1 clock periods. As described above, timing delays for ADC clock signals may reduce noise.

Figure 7:
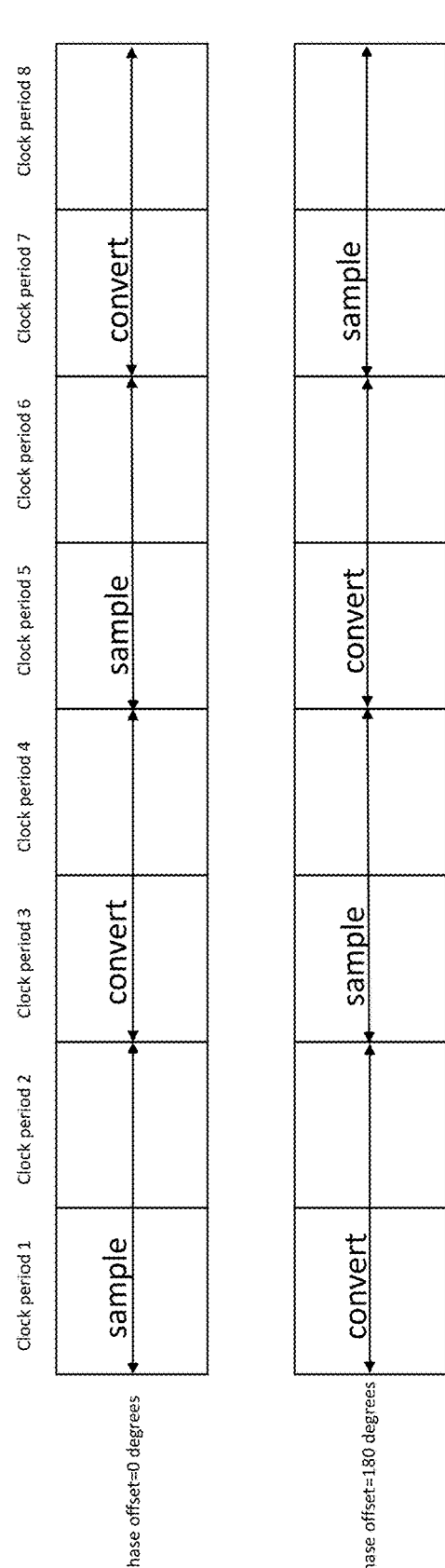
FIG. 7 illustrates an example timing diagram for two ADCs, in accordance with certain embodiments herein.

FIG. 7 illustrates an example timing diagram for two ADCs, in accordance with certain embodiments herein. As with FIG. 6, eight clock periods are shown, sampling stages are labeled "sample" and conversion stages are labeled "convert." The two ADCs have ADC clock signals having the same frequency, but one ADC clock signal has a timing delay of 0 degrees and the other ADC clock signal has a timing delay of 180 degrees. The two ADCs may be the ADC 102$_1$ and 102$_2$. In FIG. 7, the ADC clock signals have a frequency that is $f_{clk}/4$, where $f_{clk}$ is the frequency of a system clock. Each clock period illustrated in FG. 6 is one clock period of the system clock. As illustrated in FIG. 6, the sampling stage for a given ADC occurs during 2 periods of the system clock and the conversion stage occurs during 2 periods of the system clock. The timing sequences for each ADC are offset by 2 clock periods. In general, different ADCs may have ADC clock signals having a frequency that is $f_{clk}/R$, where the sampling stage for a given ADC occurs during S (S<R) periods of the system clock and the conversion stage occurs during the following R-S periods of the system clock. The timing sequences for different ADCs may be offset by 1 to R–1 clock periods. As described above, timing delays for ADC clock signals may reduce noise. Furthermore, increasing the time period (e.g., by increasing the number of clock periods) over which sampling occurs by ADCs may also reduce noise.

Figure 8:
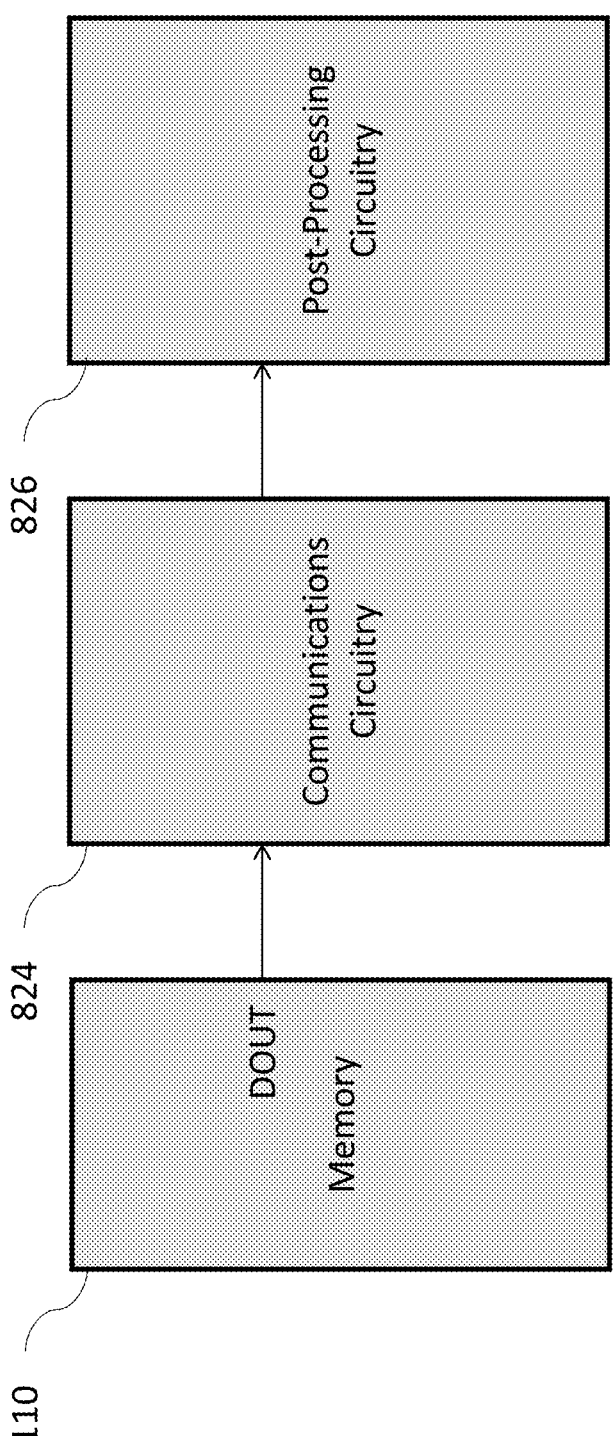
FIG. 8 illustrates an example of a downstream portion of any of the datapaths described herein, in accordance with certain embodiments described herein.

FIG. 8 illustrates an example of a downstream portion of any of the datapaths described herein, in accordance with certain embodiments described herein. The DOUT terminal of the memory 110 is coupled to the input terminal of communications circuitry 824. The output terminal of the communications circuitry 824 is coupled to the input terminal of post-processing circuitry 826. The communications circuitry 824 may be configured to transmit data from the memory 110 to the post-processing circuitry 826 and may include, for example, circuitry capable of transmitting data over a communications link such as a Universal Serial Bus (USB) communications link, a serial-deserializer (SerDes) link, or a wireless link (e.g., a link employing the IEEE 802.11 standard). Thus, the communications circuitry 824 may be coupled to the post-processing circuitry 826 through a USB communications link (e.g., a cable) or through a SerDes communications link. The post-processing circuitry 826 may be configured to post-process ultrasound data after it has been stored in the memory 110, and may include, for example, circuitry for summing, requantization, noise shaping, waveform removal, beamforming, image formation, and/or backend processing. In some embodiments, the memory 110 and the communications circuitry 824 may be located on an ultrasound-on-chip while the post-processing circuitry 826 may be located on a separate electronic device (e.g., a field-programmable gate array (FPGA) device) to which the ultrasound-on-a chip is communicatively coupled. In some embodiments, the memory 110 and the communications circuitry 824 may be located on an ultrasound probe (or ultrasound device having another form factor) while the post-processing circuitry 826 may be located on a host device to which the ultrasound probe is communicatively coupled. In some embodiments, certain functions of the post-processing circuitry 826 (e.g., beamforming) may be performed by software.

Figure 9:
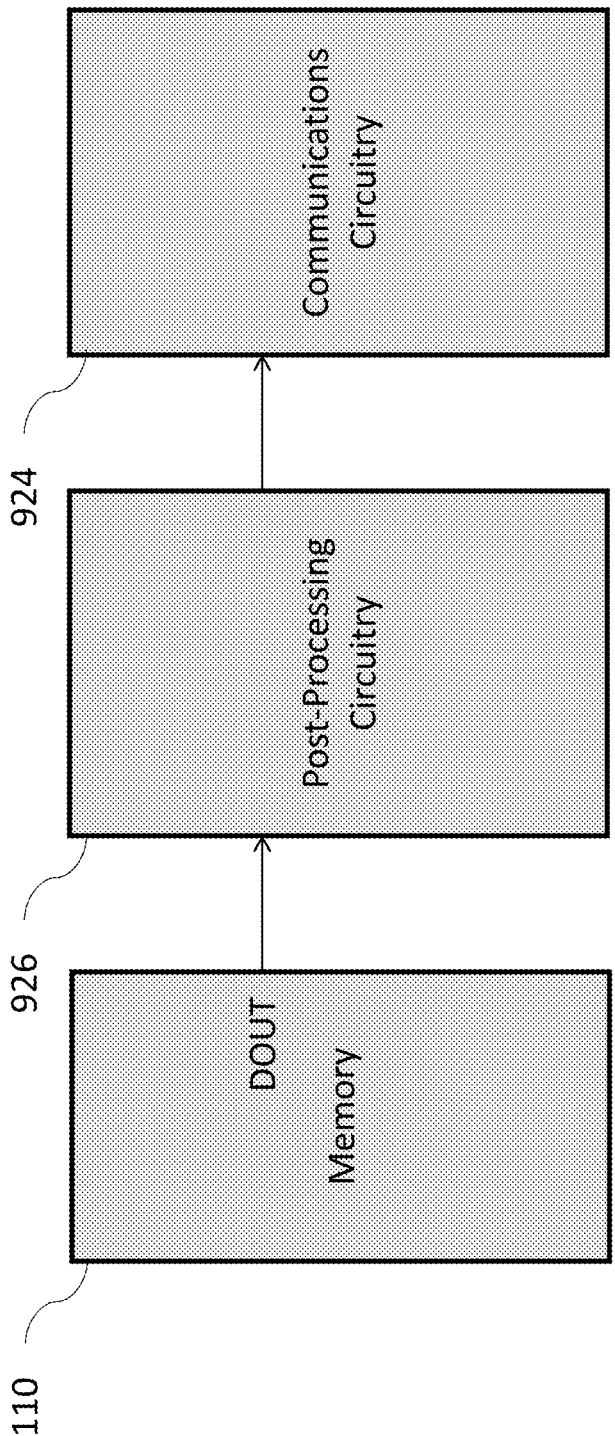
FIG. 9 illustrates an example of a downstream portion of any of the datapaths described herein, in accordance with certain embodiments described herein.

FIG. 9 illustrates another example of a downstream portion of any of the datapaths described herein, in accordance with certain embodiments described herein. The DOUT terminal of the memory 110 is coupled to the input terminal of post-processing circuitry 926. The output terminal of the post-processing circuitry 926 is coupled to the input terminal of the communications circuitry 924. The communications circuitry 924 may be configured to transmit data from the post-processing circuitry 926 to another electronic device, such as a host device or an FPGA, and may include, for example, circuitry capable of transmitting data over a communications link such as a Universal Serial Bus (USB) communications link, a serial-deserializer (SerDes) link, or a wireless link (e.g., a link employing the IEEE 802.11 standard). The post-processing circuitry 926 may be configured to post-process ultrasound data after it has been stored in the memory 110, and may include, for example, circuitry for summing, requantization, noise shaping, waveform removal, beamforming, image formation, and/or backend processing. In some embodiments, the memory 110, the post-processing circuitry 926, and the communications circuitry 924 may be located on an ultrasound-on-chip. In some embodiments, the memory 110 and the post-processing circuitry 926 may be located on an ultrasound-on-chip and the communications circuitry 924 may be located on an ultrasound probe (or an ultrasound device having another form factor) in which the ultrasound-on-chip is housed. In some embodiments, the memory 110 may be located on an ultrasound-on-chip and the post-processing circuitry 926 and communications circuitry 924 may be located on an ultrasound probe in which the ultrasound-on-chip is housed. In some embodiments, the memory 110, the post-processing circuitry 926, and the communications circuitry 924 may be located on an ultrasound probe. In some embodiments, certain functions of the post-processing circuitry 926 (e.g., beamforming) may be performed by software.

As described above, in some embodiments, rather than or in addition to correcting for ADC clock signal timing delays with delay control circuitry controlling DDS circuitry, beamforming delays used in downstream beamforming circuitry, such as beamforming circuitry in the post-processing circuitry 826 or 926, may correct for the ADC clock signal timing delays. In other words, a delay implemented by the beamforming circuitry may be the sum of the delay for correcting for the ADC clock signal and the delay for beamforming.

Figure 10:
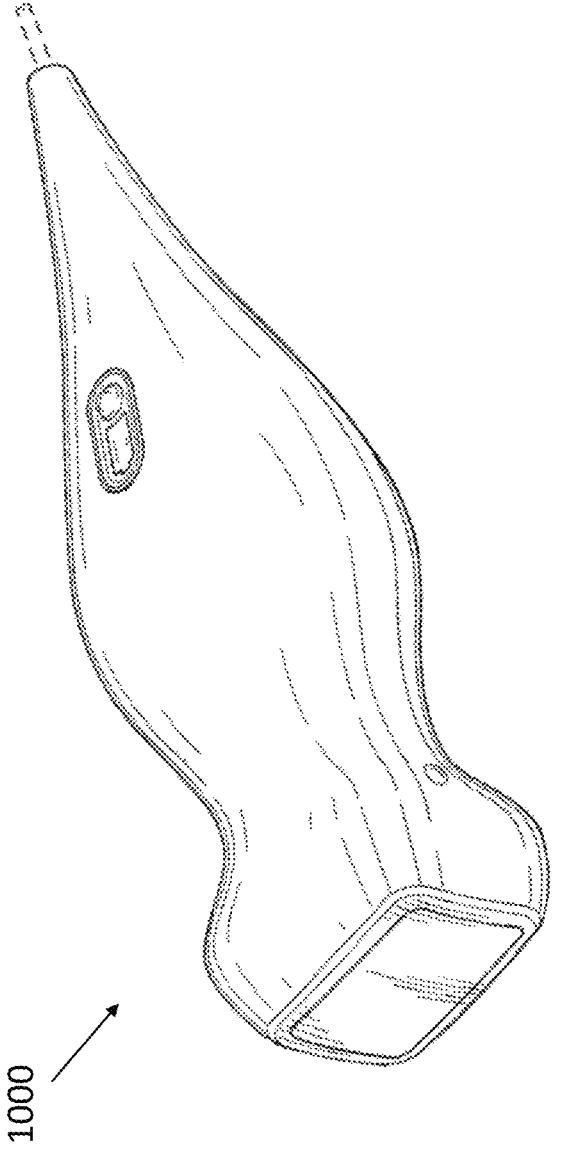
FIG. 10 illustrates an example handheld ultrasound probe in which an ultrasound-on-chip may be disposed, in accordance with certain embodiments described herein.

FIG. 10 illustrates an example handheld ultrasound probe 1000 in which an ultrasound-on-chip may be disposed, in accordance with certain embodiments described herein. The ultrasound-on-chip in the handheld ultrasound probe 1000 may include all the circuitry of any datapath described herein.

Figure 11:
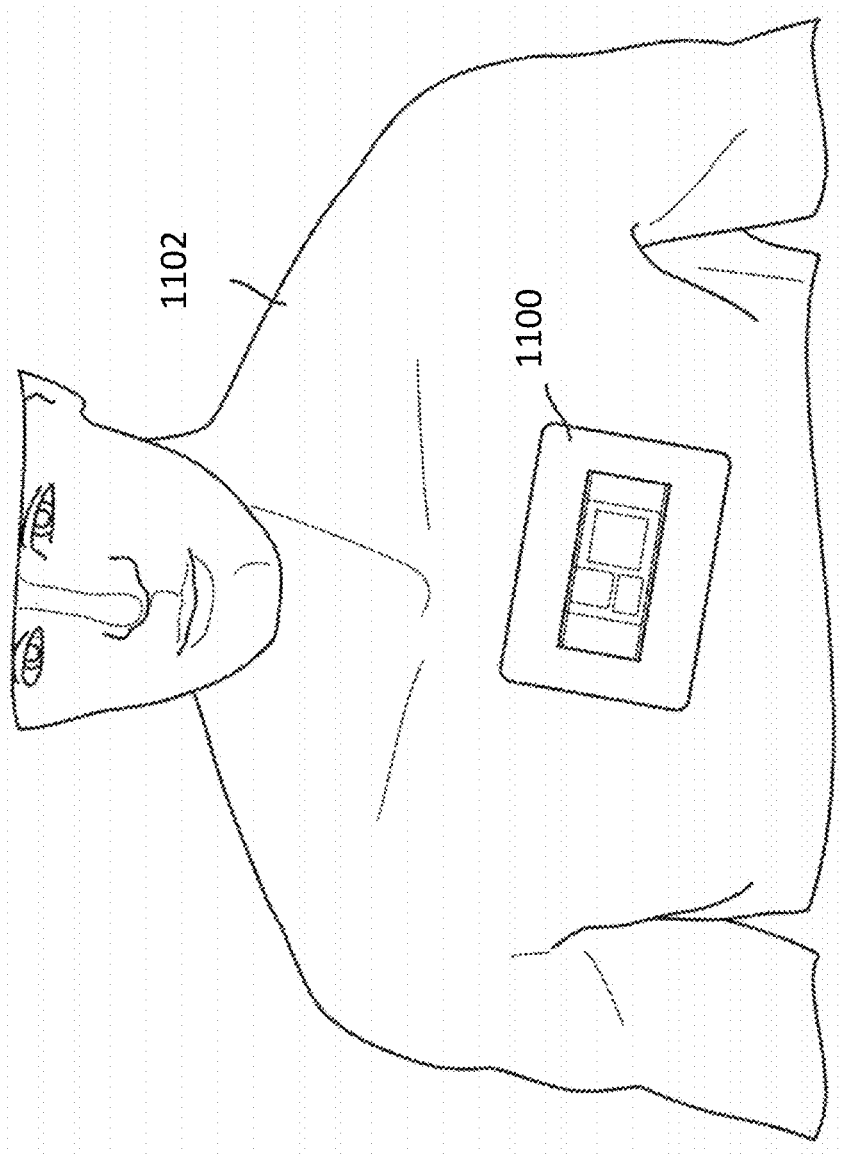
FIG. 11 illustrates an example ultrasound patch in which an ultrasound-on-chip may be disposed, in accordance with certain embodiments described herein.

FIG. 11 illustrates an example ultrasound patch 1100 in which an ultrasound-on-chip may be disposed, in accordance with certain embodiments described herein. The ultrasound patch 1100 is coupled to a subject 1102. The ultrasound-on-chip in the ultrasound patch 1100 may include all the circuitry of any datapath described herein.

Figure 12:
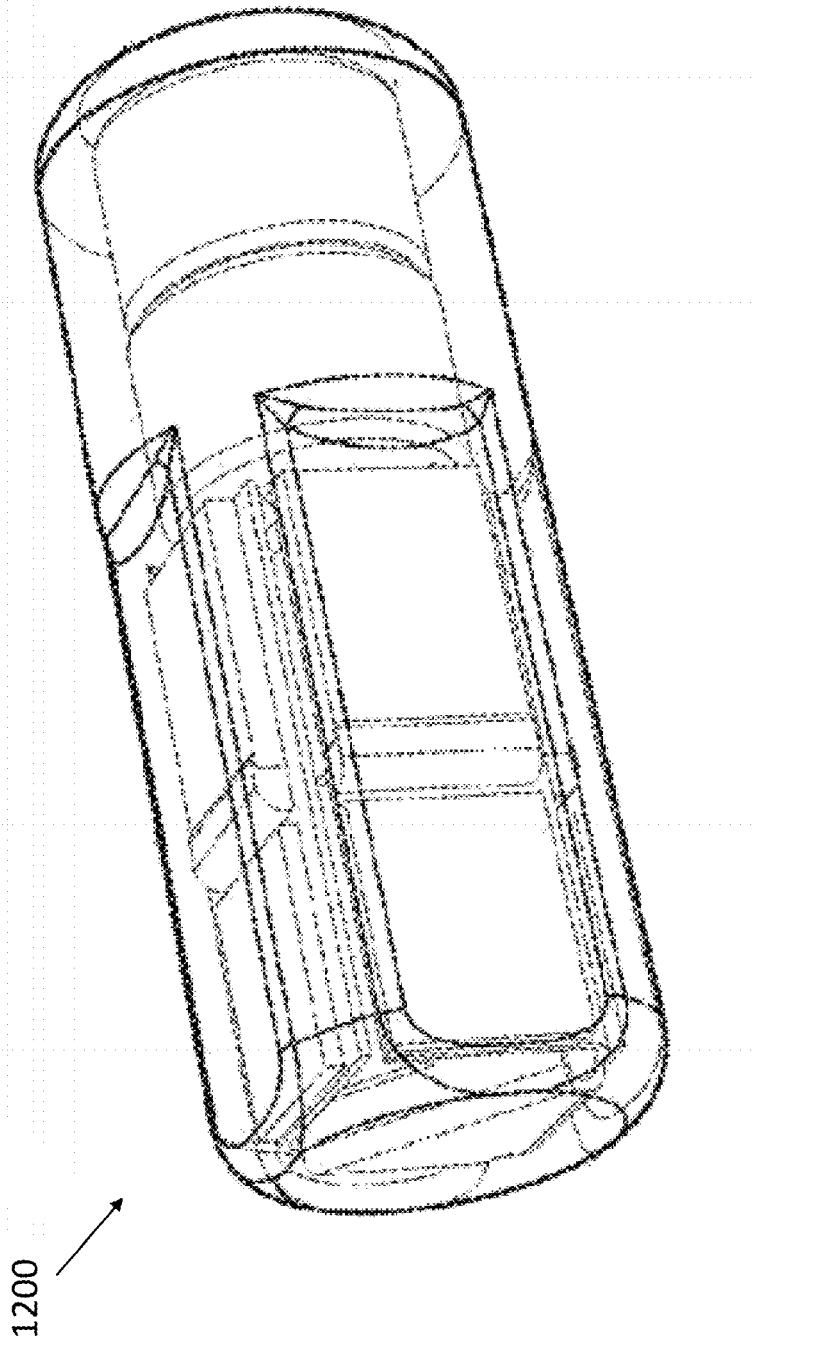
FIG. 12 illustrates an example ultrasound pill in which an ultrasound-on-chip may be disposed, in accordance with certain embodiments described herein.

FIG. 12 illustrates an example ultrasound pill 1200 in which an ultrasound-on-chip may be disposed, in accordance with certain embodiments described herein. The ultrasound-on-chip in the ultrasound patch 1200 may include all the circuitry of any datapath described herein.

Further description of the handheld ultrasound probe 1000, the ultrasound patch 1100, and the ultrasound pill 1200 may be found in U.S. patent application Ser. No. 15/626,711 titled "UNIVERSAL ULTRASOUND DEVICE AND RELATED APPARATUS AND METHODS," filed on Jun. 19, 2017 and published as U.S. Pat. App. Publication No. 2017-0360399 A1 (and assigned to the assignee of the instant application).

Figure 13:
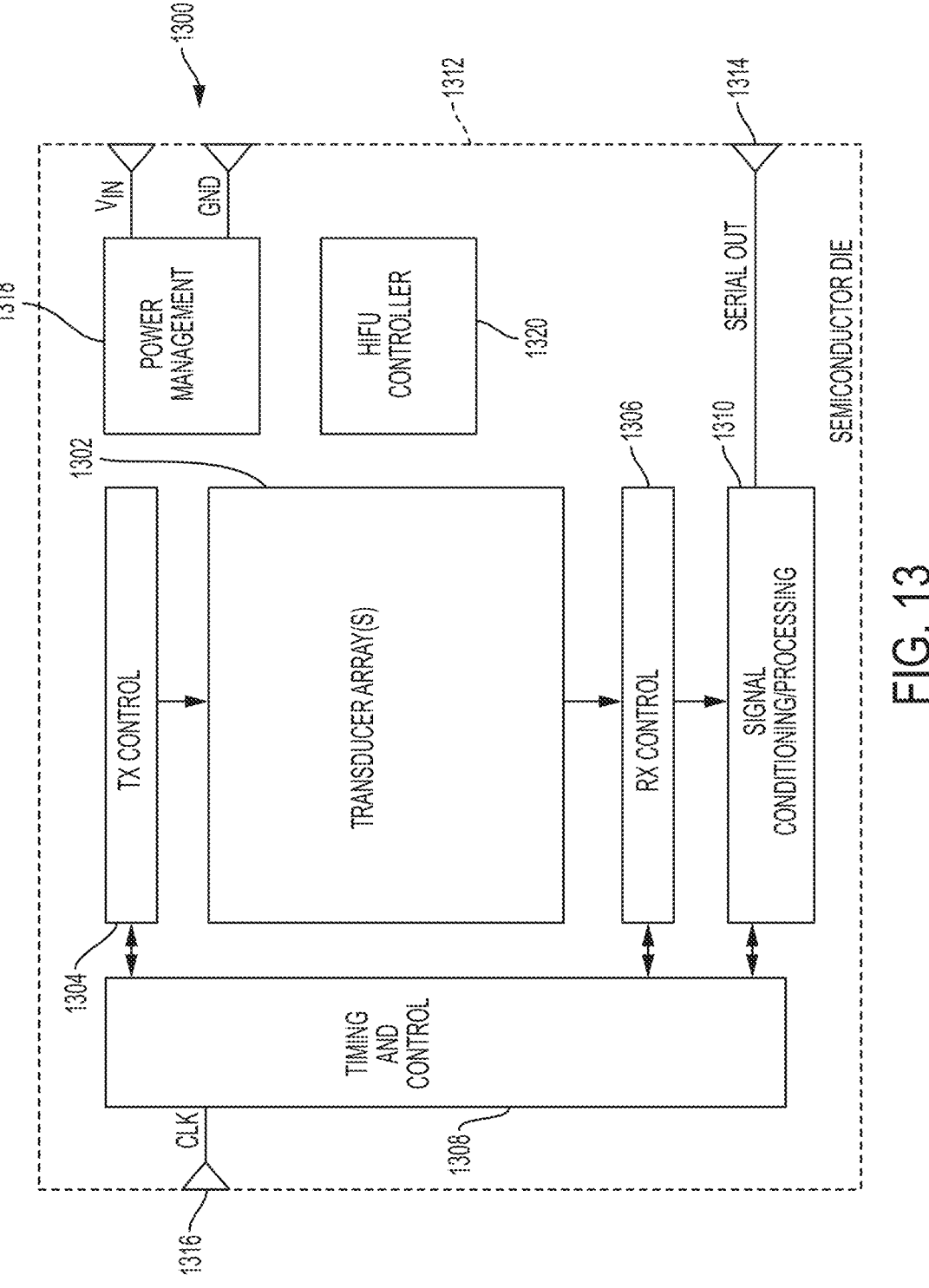
FIG. 13 illustrates a block diagram of an example ultrasound-on-chip, in accordance with certain embodiments described herein.

FIG. 13 illustrates a block diagram of an example ultrasound-on-chip, in accordance with certain embodiments described herein. As shown, the ultrasound device 1300 may include one or more transducer arrangements (e.g., arrays) 1302, transmit (TX) circuitry 1304, receive (RX) circuitry 1306, a timing and control circuit 1308, a signal conditioning/processing circuit 1310, a power management circuit 1318, and/or a high-intensity focused ultrasound (HIFU) controller 1320. In the embodiment shown, all of the illustrated elements are formed on a single semiconductor die 1312. It should be appreciated, however, that in alternative embodiments one or more of the illustrated elements may be instead located off-chip, or on multiple chips packaged together. In addition, although the illustrated example shows both TX circuitry 1304 and RX circuitry 1306, in alternative embodiments only TX circuitry or only RX circuitry may be employed. For example, such embodiments may be employed in a circumstance where one or more transmission-only devices 1300 are used to transmit acoustic signals and one or more reception-only devices 1300 are used to receive acoustic signals that have been transmitted through or reflected off of a subject being ultrasonically imaged.

It should be appreciated that communication between one or more of the illustrated components may be performed in any of numerous ways. In some embodiments, for example, one or more high-speed busses (not shown), such as that employed by a unified Northbridge, may be used to allow high-speed intra-chip communication or communication with one or more off-chip components.

The one or more transducer arrays 1302 may take on any of numerous forms, and aspects of the present technology do not necessarily require the use of any particular type or arrangement of transducer cells or transducer elements. Indeed, although the term "array" is used in this description, it should be appreciated that in some embodiments the transducer elements may not be organized in an array and may instead be arranged in some non-array fashion. In various embodiments, each of the transducer elements in the array 1302 may, for example, include one or more capacitive micromachined ultrasonic transducers (CMUTs), one or more CMOS ultrasonic transducers (CUTs), one or more piezoelectric micromachined ultrasonic transducers (PMUTs), and/or one or more other suitable ultrasonic transducer cells. In some embodiments, the transducer elements of the transducer array 1302 may be formed on the same chip as the electronics of the TX circuitry 1304 and/or RX circuitry 1306. The transducer elements 1302, TX circuitry 1304, and RX circuitry 1306 may, in some embodiments, be integrated in a single ultrasound device. In some embodiments, the single ultrasound device may be a handheld device. In other embodiments, the single ultrasound device may be embodied in a patch that may be coupled to a patient. The patch may be configured to transmit, wirelessly, data collected by the patch to one or more external devices for further processing.

A CUT may, for example, include a cavity formed in a CMOS wafer, with a membrane overlying the cavity, and in some embodiments sealing the cavity. Electrodes may be provided to create a transducer cell from the covered cavity structure. The CMOS wafer may include integrated circuitry to which the transducer cell may be connected. The transducer cell and CMOS wafer may be monolithically integrated, thus forming an integrated ultrasonic transducer cell and integrated circuit on a single substrate (the CMOS wafer).

The TX circuitry 1304 (if included) may, for example, generate pulses that drive the individual elements of, or one or more groups of elements within, the transducer array(s) 1302 so as to generate acoustic signals to be used for imaging. The RX circuitry 1306, on the other hand, may receive and process electronic signals generated by the individual elements of the transducer array(s) 1302 when acoustic signals impinge upon such elements.

In some embodiments, the timing and control circuit 1308 may, for example, be responsible for generating all timing and control signals that are used to synchronize and coordinate the operation of the other elements in the device 1300. In the example shown, the timing and control circuit 1308 is driven by a single clock signal CLK supplied to an input port 1316. The clock signal CLK may, for example, be a high-frequency clock used to drive one or more of the on-chip circuit components. In some embodiments, the clock signal CLK may, for example, be a 1.5625 GHz or 2.5 GHz clock used to drive a high-speed serial output device (not shown in FIG. 13) in the signal conditioning/processing circuit 1310, or a 20 MHz or 40 MHz clock used to drive other digital components on the semiconductor die 1312, and the timing and control circuit 1308 may divide or multiply the clock CLK, as necessary, to drive other components on the die 1312. In other embodiments, two or more clocks of different frequencies (such as those referenced above) may be separately supplied to the timing and control circuit 1308 from an off-chip source.

The power management circuit 1318 may, for example, be responsible for converting one or more input voltages VIN from an off-chip source into voltages needed to carry out operation of the chip, and for otherwise managing power consumption within the device 1300. In some embodiments, for example, a single voltage (e.g., 12V, 80V, 100V, 120V, etc.) may be supplied to the chip and the power management circuit 1318 may step that voltage up or down, as necessary, using a charge pump circuit or via some other DC-to-DC voltage conversion mechanism. In other embodiments, multiple different voltages may be supplied separately to the power management circuit 1318 for processing and/or distribution to the other on-chip components.

As shown in FIG. 13, in some embodiments, a HIFU controller 1320 may be integrated on the semiconductor die 1312 so as to enable the generation of HIFU signals via one or more elements of the transducer array(s) 1302. In other embodiments, a HIFU controller for driving the transducer array(s) 1302 may be located off-chip, or even within a device separate from the device 1300. That is, aspects of the present disclosure relate to provision of ultrasound-on-a-chip HIFU systems, with and without ultrasound imaging capability. It should be appreciated, however, that some embodiments may not have any HIFU capabilities and thus may not include a HIFU controller 1320.

Moreover, it should be appreciated that the HIFU controller 1320 may not represent distinct circuitry in those embodiments providing HIFU functionality. For example, in some embodiments, the remaining circuitry of FIG. 13 (other than the HIFU controller 1320) may be suitable to provide ultrasound imaging functionality and/or HIFU, i.e., in some embodiments the same shared circuitry may be operated as an imaging system and/or for HIFU. Whether or not imaging or HIFU functionality is exhibited may depend on the power provided to the system. HIFU typically operates at higher powers than ultrasound imaging. Thus, providing the system a first power level (or voltage level) appropriate for imaging applications may cause the system to operate as an imaging system, whereas providing a higher power level (or voltage level) may cause the system to operate for HIFU. Such power management may be provided by off-chip control circuitry in some embodiments.

In addition to using different power levels, imaging and HIFU applications may utilize different waveforms. Thus, waveform generation circuitry may be used to provide suitable waveforms for operating the system as either an imaging system or a HIFU system.

In some embodiments, the system may operate as both an imaging system and a HIFU system (e.g., capable of providing image-guided HIFU). In some such embodiments, the same on-chip circuitry may be utilized to provide both functions, with suitable timing sequences used to control the operation between the two modalities.

In the example shown, one or more output ports 1314 may output a high-speed serial data stream generated by one or more components of the signal conditioning/processing circuit 1310. Such data streams may, for example, be generated by one or more USB 3.0 modules, and/or one or more 10 GB, 40 GB, or 100 GB Ethernet modules, integrated on the semiconductor die 1312. In some embodiments, the signal stream produced on output port 1314 can be fed to a computer, tablet, or smartphone for the generation and/or display of 2-dimensional, 3-dimensional, and/or tomographic images. In embodiments in which image formation capabilities are incorporated in the signal conditioning/processing circuit 1310, even relatively low-power devices, such as smartphones or tablets which have only a limited amount of processing power and memory available for application execution, can display images using only a serial data stream from the output port 1314. As noted above, the use of on-chip analog-to-digital conversion and a high-speed serial data link to offload a digital data stream is one of the features that helps facilitate an "ultrasound on a chip" solution according to some embodiments of the technology described herein.

Devices 1300 such as that shown in FIG. 13 may be used in any of a number of imaging and/or treatment (e.g., HIFU) applications, and the particular examples discussed herein should not be viewed as limiting. In one illustrative implementation, for example, an imaging device including an N×M planar or substantially planar array of CMUT elements may itself be used to acquire an ultrasonic image of a subject, e.g., a person's abdomen, by energizing some or all of the elements in the array(s) 1302 (either together or individually) during one or more transmit phases, and receiving and processing signals generated by some or all of the elements in the array(s) 1302 during one or more receive phases, such that during each receive phase the CMUT elements sense acoustic signals reflected by the subject. In other implementations, some of the elements in the array(s) 1302 may be used only to transmit acoustic signals and other elements in the same array(s) 1302 may be simultaneously used only to receive acoustic signals. Moreover, in some implementations, a single imaging device may include a P×Q array of individual devices, or a P×Q array of individual N×M planar arrays of CMUT elements, which components can be operated in parallel, sequentially, or according to some other timing scheme so as to allow data to be accumulated from a larger number of CMUT elements than can be embodied in a single device 1300 or on a single die 1312.

In yet other implementations, a pair of imaging devices can be positioned so as to straddle a subject, such that one or more CMUT elements in the device(s) 1300 of the imaging device on one side of the subject can sense acoustic signals generated by one or more CMUT elements in the device(s) 1300 of the imaging device on the other side of the subject, to the extent that such pulses were not substantially attenuated by the subject. Moreover, in some implementations, the same device 1300 can be used to measure both the scattering of acoustic signals from one or more of its own CMUT elements as well as the transmission of acoustic signals from one or more of the CMUT elements disposed in an imaging device on the opposite side of the subject.

Various inventive concepts may be embodied as one or more processes, of which examples have been provided. The acts performed as part of each process may be ordered in any suitable way. Thus, embodiments may be constructed in which acts are performed in an order different than illustrated, which may include performing some acts simultaneously, even though shown as sequential acts in illustrative embodiments. Further, one or more of the processes may be combined and/or omitted, and one or more of the processes may include additional steps.

Various aspects of the present disclosure may be used alone, in combination, or in a variety of arrangements not specifically described in the embodiments described in the foregoing and is therefore not limited in its application to the details and arrangement of components set forth in the foregoing description or illustrated in the drawings. For example, aspects described in one embodiment may be combined in any manner with aspects described in other embodiments.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more"

of the elements so conjoined. Other elements may optionally be present other than the elements specifically identified by the "and/or" clause, whether related or unrelated to those elements specifically identified.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

As used herein, reference to a numerical value being between two endpoints should be understood to encompass the situation in which the numerical value can assume either of the endpoints. For example, stating that a characteristic has a value between A and B, or between approximately A and B, should be understood to mean that the indicated range is inclusive of the endpoints A and B unless otherwise noted.

The terms "approximately" and "about" may be used to mean within ±20% of a target value in some embodiments, within ±10% of a target value in some embodiments, within ±5% of a target value in some embodiments, and yet within ±2% of a target value in some embodiments. The terms "approximately" and "about" may include the target value.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Having described above several aspects of at least one embodiment, it is to be appreciated various alterations, modifications, and improvements will readily occur to those skilled in the art. Such alterations, modifications, and improvements are intended to be object of this disclosure. Accordingly, the foregoing description and drawings are by way of example only.

What is claimed is:

1. An ultrasound device, comprising:
a plurality of ultrasonic transducers incorporated together on an integrated circuit chip or one or more integrated circuit chips packaged together, the plurality of ultrasonic transducers being configured to obtain analog ultrasound echo signals for use in generating ultrasound images;
a first plurality of analog-to-digital converters (ADC) coupled to a first set of the plurality of ultrasonic transducers and configured to operate with a same first ADC clock signal having a first timing delay;
a second plurality of ADCs coupled to a second set of the plurality of ultrasonic transducers and configured to operate with a same second ADC clock signal having a second timing delay different than the first timing delay; and digital processing circuitry configured to process digital ultrasound data from the first and second pluralities of ADCs;
wherein the first timing delay and the second timing delay differ by a fraction of a sampling clock period such that sample-and-hold operations of the first plurality of ADCs and the second plurality of ADCs begin at different times within the sampling clock period to reduce sampling-related noise; and wherein the digital processing circuitry is configured to compensate for the different times of the sample-and-hold operations by applying a digital delay to the digital ultrasound data that is substantially equal to an amount of time represented by the first or second timing delay but in an opposite time direction.

2. The ultrasound device of claim 1, wherein the first plurality of ADCs is configured to operate with the first ADC clock signal and the second plurality of ADCs is configured to operate with the second ADC clock signal, such that sample and hold operations of the first plurality of ADCs and the second plurality of ADCs start at times that are different by a fraction of a sampling clock period.

3. The ultrasound device of claim 1, wherein the first plurality of ADCs is in one ultrasound processing unit (UPU) and the second plurality of ADCs is in another UPU.

4. The ultrasound device of claim 1, wherein the first plurality of ADCs and the second plurality of ADCs are in a single ultrasound processing unit (UPU).

5. The ultrasound device of claim 1, further comprising:
first clocking circuitry configured to provide the first ADC clock signal to the first plurality of ADCs; and
second clocking circuitry configured to provide the second ADC clock signal to the second plurality of ADCs.

6. The ultrasound device of claim 1, further comprising:
clocking circuitry configured to provide the first ADC clock signal to the first plurality of ADCs and the second ADC clock signal to the second plurality of ADCs.

7. The ultrasound device of claim 1, wherein the first ADC clock signal and the second ADC clock signal are derived from a system clock.

8. The ultrasound device of claim 1, wherein the first ADC clock signal and the second ADC clock signal are generated by a phase-locked loop (PLL).

9. The ultrasound device of claim 1, wherein the first ADC clock signal and the second ADC clock signal have a same frequency.

10. The ultrasound device of claim 1, further comprising:
first direct digital synthesis (DDS) circuitry;
first delay control circuitry configured to control the first DDS circuitry to implement a first delay in the digital ultrasound data from the first plurality of ADCs;
second DDS circuitry; and
second delay control circuitry configured to control the second DDS circuitry to implement a second delay in the digital ultrasound data from the second plurality of ADCs;
wherein the first delay and the second delay are different.

11. The ultrasound device of claim 1, further comprising:
direct digital synthesis (DDS) circuitry; and
delay control circuitry configured to control the DDS circuitry to implement a first delay in the digital ultrasound data from the first plurality of ADCs and a second delay in the digital ultrasound data from the second plurality of ADCs.

12. The ultrasound device of claim 11, wherein:

the first delay corrects for the first timing delay; and the second delay corrects for the second timing delay.

13. The ultrasound device of claim 11, wherein:

an amount of the first delay is substantially equal to an amount of time represented by the first timing delay and in an opposite time direction; and an amount of the second delay is substantially equal to an amount of time represented by the second timing delay and in an opposite time direction.

14. The ultrasound device of claim 11, wherein:

the first delay includes a delay for correcting for the first timing delay and a delay for beamforming the digital ultrasound data from the first plurality of ADCs; and the second delay includes a delay for correcting for the second timing delay and a delay for beamforming the digital ultrasound data from the second plurality of ADCs.

15. The ultrasound device of claim 11, wherein:

the first timing delay represents a delay forward in time and the first delay is backward in time; or the first timing delay represents a delay backward in time and the first delay is forward in time.

16. The ultrasound device of claim 1, further comprising:

beamforming circuitry configured to implement a first delay in the digital ultrasound data from the first plurality of ADCs and a second delay in the digital ultrasound data from the second plurality of ADCs;

wherein the first delay and the second delay are different.

17. The ultrasound device of claim 16, wherein:

the first delay includes a delay for correcting for the first timing delay and a delay for beamforming the digital ultrasound data from the first plurality of ADCs; and the second delay includes a delay for correcting for the second timing delay and a delay for beamforming the digital ultrasound data from the second plurality of ADCs.

18. The ultrasound device of claim 17, wherein interpolation filters, linear interpolation, or fractional delay filters are used to correct for the first timing delay and the second timing delay.

19. The ultrasound device of claim 1, wherein the first plurality of ADCs and the second plurality of ADCs are configured to operate simultaneously using the first ADC clock signal and the second ADC clock signal, respectively.

20. The ultrasound device of claim 1, wherein the first ADC clock signal and the second ADC clock signal are strobe signals.

21. The ultrasound device of claim 1, wherein the ultrasound device comprises an ultrasound-on-chip.

22. The ultrasound device of claim 21, wherein the ultrasound-on-chip comprises the first plurality of ADCs and the second plurality of ADCs and a plurality of ultrasonic transducers.

23. The ultrasound device of claim 1, wherein the ultrasound device comprises an ultrasound-on-chip including hundreds of ADCs, thousands of ADCs, or tens of thousands of ADCs.

* * * * *